(12) United States Patent
Li et al.

(10) Patent No.: US 11,961,002 B2
(45) Date of Patent: Apr. 16, 2024

(54) RANDOM SELECTION OF OBSERVATION CELLS FOR PROXY MODELING OF REACTIVE TRANSPORT MODELING

(71) Applicant: Saudi Arabian Oil Company, Dhahran (SA)

(72) Inventors: Yupeng Li, Beijing (CN); Peng Lu, Dammam (SA)

(73) Assignee: Saudi Arabian Oil Company, Dhahran (SA)

(*) Notice: Subject to any disclaimer, the term of this patent is extended or adjusted under 35 U.S.C. 154(b) by 324 days.

(21) Appl. No.: 16/810,124

(22) Filed: Mar. 5, 2020

(65) Prior Publication Data

US 2021/0279593 A1    Sep. 9, 2021

(51) Int. Cl.
| | | |
|---|---|---|
| G06N 3/08 | (2006.01) | |
| G01V 99/00 | (2024.01) | |
| G06N 3/045 | (2023.01) | |
| G16C 20/30 | (2019.01) | |
| G16C 20/70 | (2019.01) | |

(52) U.S. Cl.
CPC .......... *G16C 20/70* (2019.02); *G01V 99/005* (2013.01); *G06N 3/045* (2023.01); *G16C 20/30* (2019.02)

(58) Field of Classification Search
CPC ...... G01V 99/005; G06F 30/27; G06N 20/00; G06N 3/084; G16C 20/10; G16C 20/30; G16C 20/70; G16C 60/00
USPC .......................................................... 706/25
See application file for complete search history.

(56) References Cited

U.S. PATENT DOCUMENTS

| 5,576,755 A | 11/1996 | Davis et al. |
| D640,264 S | 6/2011 | Fujii et al. |
| 8,046,314 B2 * | 10/2011 | Graf ............ E21B 44/00 |
| | | 706/15 |

(Continued)

FOREIGN PATENT DOCUMENTS

| EP | 3246818 | 11/2017 |
| WO | WO 2019055565 | 3/2019 |
| WO | WO 2019241062 | 12/2019 |

OTHER PUBLICATIONS

De Lucia, M.; Kempka, T.; Jatnieks, J.; Kühn, M. Integrating Surrogate Models into Subsurface Simulation Framework Allows Computation of Complex Reactive Transport Scenarios. Energy Procedia 2017, 125, 580-587.*

(Continued)

*Primary Examiner* — Soren Harward
(74) *Attorney, Agent, or Firm* — Fish & Richardson P.C.

(57) ABSTRACT

Systems and methods include a computer-implemented method for random selection and use of observation cells. Observation cells are randomly selected from a model of process-based reactive transport modeling (RTM). The observation cells are incorporated into a neural network for proxy modeling. A set of parameter-specific proxy models represented by a neural network is trained. Each parameter-specific proxy model corresponds to a specific RTM parameter from a set of RTM parameters. Blind tests are performed using the set of parameter-specific proxy models, where each blind test tests a specific one of the parameter-specific proxy models. Predictions are generated using the set of parameter-specific proxy models. 3-dimensional interpolation the observation cells is performed.

20 Claims, 26 Drawing Sheets

(56) References Cited

U.S. PATENT DOCUMENTS

| | | | |
|---|---|---|---|
| D656,945 S | 4/2012 | Lee et al. | |
| 8,489,632 B1* | 7/2013 | Breckenridge | G06F 18/25 |
| | | | 707/777 |
| 8,688,426 B2 | 4/2014 | Al-Shammari | |
| 9,134,457 B2* | 9/2015 | Hurley | G01V 99/005 |
| 9,183,676 B2 | 11/2015 | McCulloch | |
| D761,828 S | 7/2016 | Koeten et al. | |
| D766,285 S | 9/2016 | Yang | |
| 10,049,172 B2* | 8/2018 | Zhang | G01V 99/005 |
| D842,881 S | 3/2019 | Thesman | |
| D847,170 S | 4/2019 | Lirov et al. | |
| D878,403 S | 3/2020 | Watson et al. | |
| 10,750,992 B2 | 8/2020 | Fan | |
| D896,828 S | 9/2020 | Linares et al. | |
| 10,853,533 B2* | 12/2020 | Plateaux | G06F 30/20 |
| D930,025 S * | 9/2021 | Li | G06N 20/00 |
| | | | D14/486 |
| 2004/0006530 A1 | 1/2004 | Allamon | |
| 2009/0020284 A1* | 1/2009 | Graf | E21B 44/00 |
| | | | 166/250.15 |
| 2012/0136194 A1 | 5/2012 | Zhang | |
| 2012/0221306 A1* | 8/2012 | Hurley | G01V 99/005 |
| | | | 703/6 |
| 2012/0284600 A1* | 11/2012 | Lin | G06F 40/18 |
| | | | 715/212 |
| 2014/0164005 A1 | 6/2014 | Merkin | |
| 2014/0214379 A1* | 7/2014 | Bethke | G16C 20/10 |
| | | | 703/2 |
| 2015/0227278 A1 | 8/2015 | Bruce et al. | |
| 2016/0110657 A1* | 4/2016 | Gibiansky | G06N 20/00 |
| | | | 706/12 |
| 2016/0189426 A1 | 6/2016 | Thomas | |
| 2017/0169139 A1* | 6/2017 | Zhang | G06F 30/20 |
| 2017/0321543 A1* | 11/2017 | Plateaux | G06F 30/20 |
| 2018/0376534 A1 | 12/2018 | Mustafic | |
| 2019/0065957 A1 | 2/2019 | Movshovitz-Attias | |
| 2019/0282178 A1 | 9/2019 | Volosin et al. | |
| 2019/0333199 A1 | 10/2019 | Ozcan et al. | |
| 2019/0370146 A1 | 12/2019 | Babu | |
| 2020/0008680 A1* | 1/2020 | Ohbayashi | G01B 9/02091 |
| 2020/0097847 A1* | 3/2020 | Convertino et al. | |
| | | | G06F 11/3447 |
| 2020/0341976 A1 | 10/2020 | Aggarwal | |
| 2021/0010796 A1* | 1/2021 | Ishikawa | G01N 15/1463 |
| 2021/0278935 A1* | 9/2021 | Li | G01V 99/005 |
| 2021/0279592 A1* | 9/2021 | Li | G06N 20/00 |
| 2021/0279593 A1* | 9/2021 | Li | G16C 20/70 |
| 2022/0000373 A1* | 1/2022 | Costa | A61B 5/0022 |
| 2022/0243575 A1 | 8/2022 | Kristensen | |

OTHER PUBLICATIONS

Jatnieks, J.; De Lucia, M.; Dransch, D.; Sips, M. Data-Driven Surrogate Model Approach for Improving the Performance of Reactive Transport Simulations. Energy Procedia 2016, 97, 447-453.*

Kuhn, M. Package "caret" v6.0-70, 2016.*

Laloy, E.; Jacques, D. Emulation of CPU-Demanding Reactive Transport Models: A Comparison of Gaussian Processes, Polynomial Chaos Expansion, and Deep Neural Networks. Computational Geosciences 2019, 23 (5), 1193-1215.*

Leal, A. M. M.; Kulik, D. A.; Smith, W. R.; Saar, M. O. An Overview of Computational Methods for Chemical Equilibrium and Kinetic Calculations for Geochemical and Reactive Transport Modeling. Pure and Applied Chemistry 2017, 89 (5), 597-643.*

Steefel, C. I., et al. Reactive Transport Codes for Subsurface Environmental Simulation. Computational Geosciences 2015, 19 (3), 445-478.* van der Lee, J.; De Windt, L.; Lagneau, V.; Goblet, P. Module-Oriented Modeling of Reactive Transport with HYTEC. Computers & Geosciences 2003, 29 (3), 265-275.* community.devexpress.com [online] "WinForms Layout Control: Design-time templates" Dec. 2014, retrieved on May 14, 2021, retrieved from URL <https://community.devexpress.com/blogs/ctodx/archive/2014/12/22/winforms-layout-control-design-time-templates.aspx>.

petroclass.coml [online] "PetroClass FlowTest" Jun. 2019, retrieved on May 14, 2021, retrieved from URL <http://petroclass.com/FlowTest.html>.

PCT International Search Report and Written Opinion in International Appln. No. PCT/US2021/021084, dated Jun. 18, 2021, 15 pages.

PCT International Search Report and Written Opinion in International Appln. No. PCT/US2021/021085, dated Jun. 24, 2021, 15 pages.

De Lucia et al, "Integrating surrogate models into subsurface simulation framework allows simulation framework allows computation of complex reactive transport scenarios," Energy Procedia, Science Direct, Sep. 2017, XP055813606, 125:580-587, 8 pages.

Jatnieks et al., "Data-driven Surrogate Model Approach for Improving the Performance of Reactive Transport Simulations," Energy Procedia, Elsevier, NL, Nov. 2016, 97: 447-453, XP029830207, 7 pages.

Laloy et al., "Emulation of CPU-demanding reactive transport models: a comparison of Gaussian processes, polynomial chaos expansion, and deep neural networks," Computational Geosciences, Baltzer Science Publishers, Bussum, NL, Aug. 2019, 23(5): 1193-1215, 23 pages.

Zhou et al., "An adaptive Kriging surrogate method for efficient joint estimation of hydraulic and biochemical parameters in reactive transport modeling," Contaminant Hydrology, Elsevier, Amsterdam, NL, Aug. 2018, XP085466885 8 pages.

De Lucia et al, "A coupling alternative to reactive transport simulations for long-term prediction of chemical reactions in heterogeneous CO2 storage systems," Geosci. Model Dev., 8, pp. 279-294, Feb. 2015, 16 pages.

Dieuleveult et al, "A global strategy for solving reactive transport equations," Journal of Computational Physics, 228, 2009, pp. 6395-6410, 16 pages.

Erhel et al, "Characterizations of solutions in geochemistry: existence, uniqueness, and precipitation diagram," Computational Geosciences, Springer Verlag, 23, 3, pp. 523-535, Dec. 2018, 13 pages.

Leal et al, "An overview of computational methods for geochemical and reactive transport modeling," Pure Appl. Chem, 2017, vol. 89, No. 5, pp. 597-643, 47 pages.

Leal et al, "Ultra-Fast Reactive transport simulations when chemical reactions meet Machine learning: Chemical Equilibrium," arXiv:1708.04825, Aug. 2017, 25 pages.

Lu et al, "Reactive transport modelling of reflux dolomitization in the Arab-D reservoir, Ghawar field, Saudi Arabia," The Journal of International Association of Sedimentologisits, Sedimentology, 2016, 63, pp. 865-892, 28 pages.

Razavi et al, "Review of Surrogate Modeling in Water Resources," Water Resources Research, 48, Jul. 2012, 93 pages.

Turner et al, "Simulation of chemical reaction equilibria and kinetics in heterogeneous carbon micropores," Applied Surface Science 196, 2002, pp. 366-374, 9 pages.

Yapparova et al, "Reactive transport modelling of hydrothermal dolomitisation using the CSMP++GEM coupled code: Effects of temperature and geological heterogeneity," Chemical Geology, 466, pp. 562-574, Jul. 2017, 26 pages.

Agar et al., "Fundamental controls on fluid flow in carbonates: current workflows to emerging technologies," The Geological Society of London, Special Publications, 2015, 406: 1-59, 59 pages.

* cited by examiner

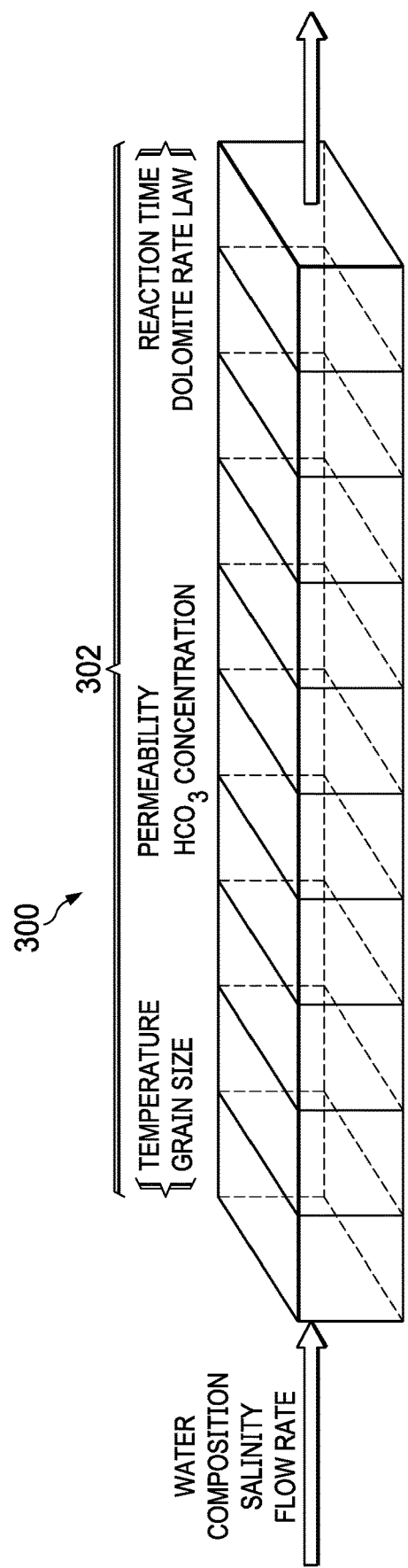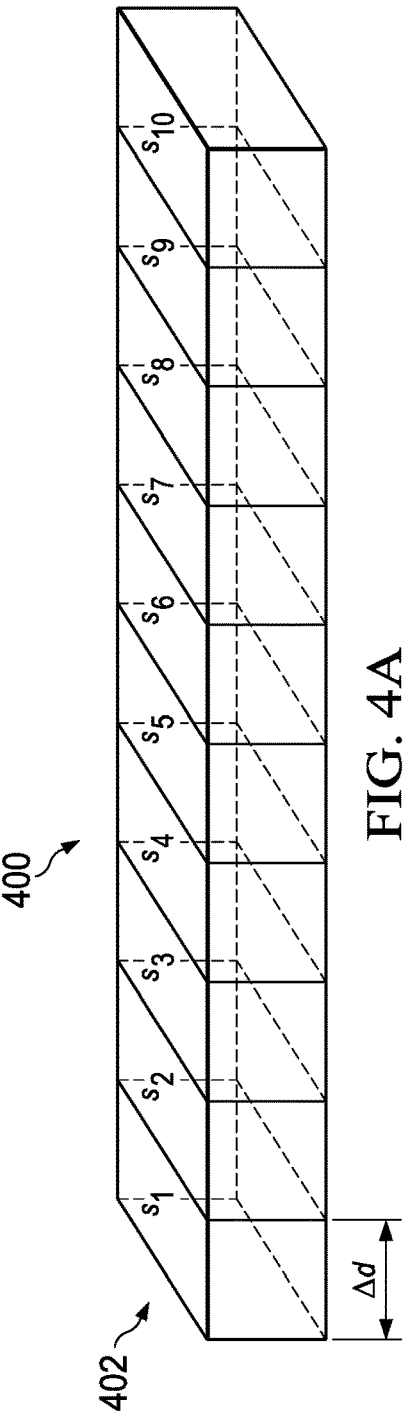

| | Simulated Steps | Total_steps | Percent (%) | Situation |
|---|---|---|---|---|
| 1 | 0 | 50 | 0 | 0 not run yet |
| 2 | 0 | 50 | 0 | 0 not run yet |
| 3 | 0 | 50 | 0 | 0 not run yet |
| 4 | 0 | 50 | 0 | 0 not run yet |
| 5 | 0 | 50 | 0 | 0 not run yet |
| 6 | 0 | 50 | 0 | 0 not run yet |
| 7 | 0 | 50 | 0 | 0 not run yet |
| 8 | 0 | 50 | 0 | 0 not run yet |
| 9 | 0 | 50 | 0 | 0 not run yet |
| 10 | 0 | 50 | 0 | 0 not run yet |
| 11 | 0 | 50 | 0 | 0 not run yet |
| 12 | 0 | 50 | 0 | 0 not run yet |
| 13 | 0 | 50 | 0 | 0 not run yet |
| 14 | 0 | 50 | 0 | 0 not run yet |
| 15 | 0 | 50 | 0 | 0 not run yet |
| 16 | 0 | 50 | 0 | 0 not run yet |
| 17 | 0 | 50 | 0 | 0 not run yet |
| 18 | 0 | 50 | 0 | 0 not run yet |
| 19 | 0 | 50 | 0 | 0 not run yet |
| 20 | 0 | 50 | 0 | 0 not run yet |
| 21 | 0 | 50 | 0 | 0 not run yet |
| 22 | 0 | 50 | 0 | 0 not run yet |

FIG. 10B

| | Simulated Steps | Total_steps | Percent (%) | Situation |
|---|---|---|---|---|
| 1 | 0 | 50 | 0 | 0 not run yet |
| 2 | 0 | 50 | 0 | 0 not run yet |
| 3 | 0 | 50 | 0 | 0 not run yet |
| 4 | 12 | 50 | 24 | need to run longer |
| 5 | 0 | 50 | 0 | 0 not run yet |
| 6 | 8 | 50 | 16 | need to run longer |
| 7 | 28 | 50 | 56 | need to run longer |
| 8 | 28 | 50 | 56 | need to run longer |
| 9 | 0 | 50 | 0 | 0 not run yet |
| 10 | 0 | 50 | 0 | 0 not run yet |
| 11 | 5 | 50 | 10 | need to run longer |
| 12 | 28 | 50 | 56 | need to run longer |
| 13 | 0 | 50 | 0 | 0 not run yet |
| 14 | 0 | 50 | 0 | 0 not run yet |
| 15 | 4 | 50 | 8 | need to run longer |
| 16 | 28 | 50 | 56 | need to run longer |
| 17 | 0 | 50 | 0 | 0 not run yet |
| 18 | 0 | 50 | 0 | 0 not run yet |
| 19 | 0 | 50 | 0 | 0 not run yet |
| 20 | 5 | 50 | 10 | need to run longer |
| 21 | 0 | 50 | 0 | 0 not run yet |
| 22 | 0 | 50 | 0 | 0 not run yet |

FIG. 10C

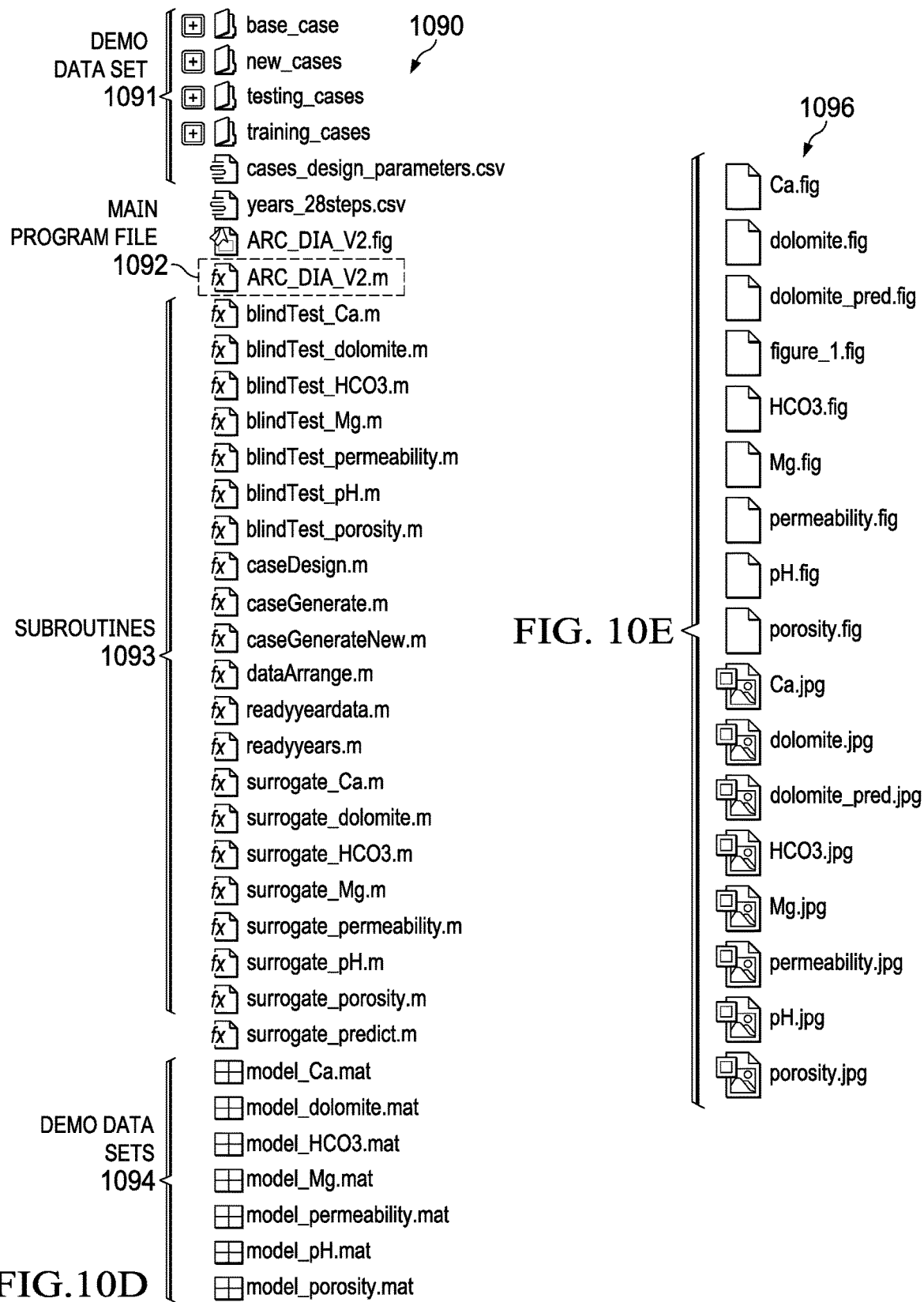

RANDOM SELECTION OF OBSERVATION CELLS FOR PROXY MODELING OF REACTIVE TRANSPORT MODELING

BACKGROUND

The present disclosure applies to reactive transport modeling (RTM). RTM techniques can include the use of computer models modeling interactions associated with chemical reactions and the transportation of fluids through the Earth's crust. For example, the models can be used to predict the distribution of chemical reactions that occur relative to space and time.

SUMMARY

The present disclosure describes techniques that can be used for developing a workflow and computer program for a machine learning-based proxy model used as a surrogate for process-based reactive transport modeling (RTM). Using a training data set generated from RTM, a proxy model can be developed using a neural network approach. Predicted results that are obtainable from the proxy model can be shown to agree with the original RTM.

In some implementations, a computer-implemented method for performing operations for random selection and use of observation cells includes the following. Observation cells are randomly selected from a model of process-based reactive transport modeling (RTM). The observation cells are incorporated into a neural network for proxy modeling. A set of parameter-specific proxy models represented by a neural network is trained. Each parameter-specific proxy model corresponds to a specific RTM parameter from a set of RTM parameters. Blind tests are performed using the set of parameter-specific proxy models, where each blind test tests a specific one of the parameter-specific proxy models. Predictions are generated using the set of parameter-specific proxy models. 3-dimensional interpolation the observation cells is performed.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/the instructions stored on the non-transitory, computer-readable medium.

The subject matter described in this specification can be implemented in particular implementations, so as to realize one or more of the following advantages. First, less computational time can be required as compared to process-based RTM techniques for sensitivity analysis and model calibration. Second, proxy modeling can simplify complex processes with reasonable accuracy and significantly accelerate the processes of modeling results analysis. Third, manual RTM processes can be replaced by automated processes. Fourth, an obtained proxy model can provide enough accuracy while being a computational inexpensive for model sensitivity analysis or model calibration. Fifth, the obtained proxy model can greatly accelerate the work efficiency and avoid bias that may be introduced in manual model calibration. Sixth, batch model running capabilities or parallel computations can be used for models. For example, depending on computational resources available workstations or clusters, hundreds or thousands of forward RTM models can be run simultaneously. This can reduce the time for sensitivity analysis and generate sufficient training samples for neural network analysis.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIG. 3 is a block diagram illustrating an example of a 1D dolomitization process in which several parameters are used, according to some implementations of the present disclosure.

FIG. 4A is a block diagram illustrating an example of a 1D case, according to some implementations of the present disclosure.

FIG. 10B is a screenshot of an example of a user interface (UI) that displays the status of each training case, according to some implementations of the present disclosure.

FIG. 10C is a screenshot of an example of the UI that displays the status of each training case, according to some implementations of the present disclosure.

FIG. 10D is a diagram showing examples of source code components used for proxy RTM, according to some implementations of the present disclosure.

FIG. 10E is a diagram showing examples of files used for proxy RTM, according to some implementations of the present disclosure.

Like reference numbers and designations in the various drawings indicate like elements.

DETAILED DESCRIPTION

Figure 1:
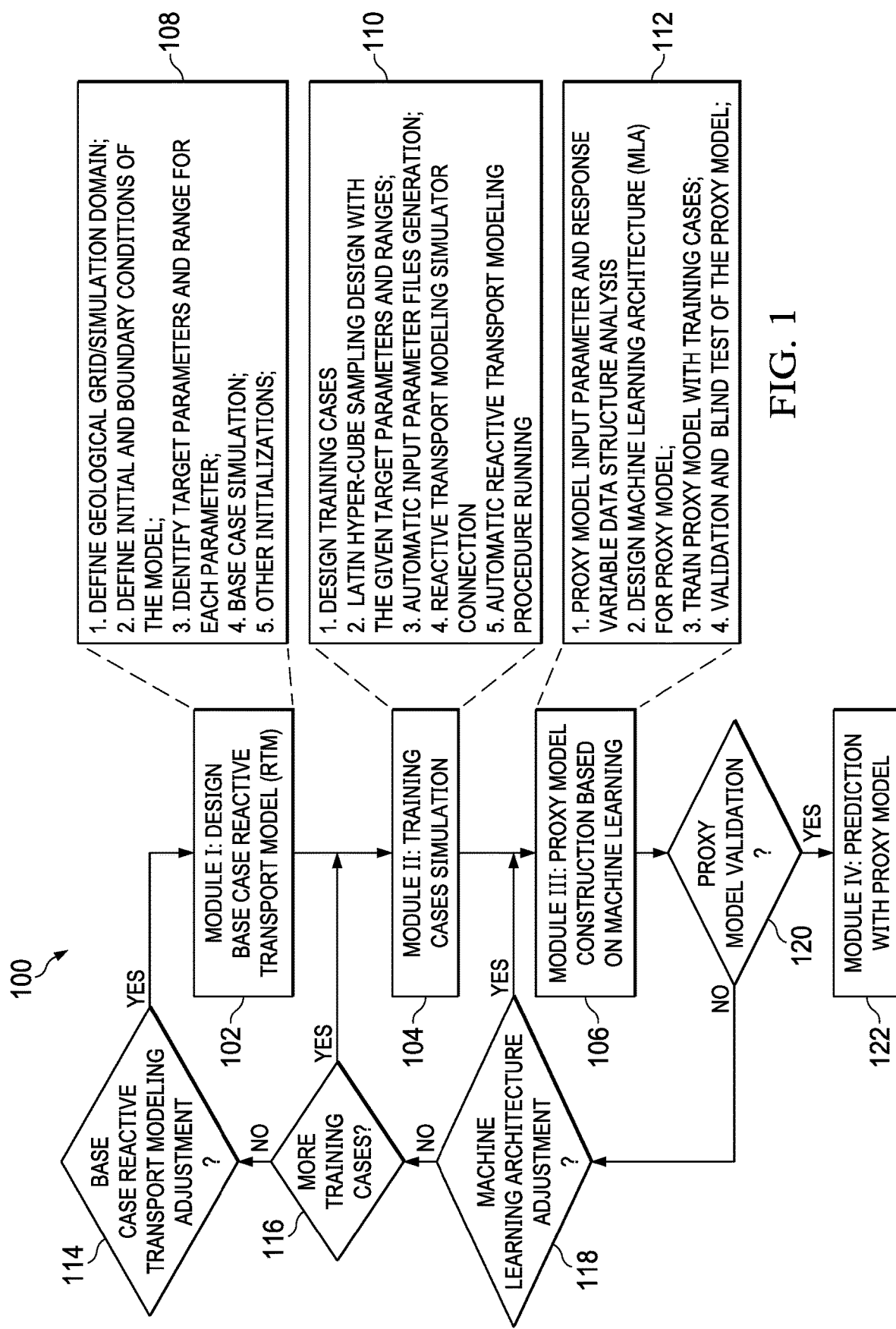
FIG. 1 is a diagram of an example of a workflow for proxy modeling, according to some implementations of the present disclosure.

The following detailed description describes techniques for training machine learning-based proxy models as surrogates for process-based reactive transport modeling (RTM). Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Proxy modeling (also known as surrogate modeling or meta-modeling) is widely used as a computational inexpensive alternative to the intensive numerical simulation in various applications. The applications can include, for example, assisted history matching in reservoir simulation in the petroleum industry. Proxy models have been widely used to assist in sensitivity analysis, risk analysis, model quantitative interpretation, and model calibration. During model calibration, for example, when complex non-linear relationships exist between input parameters and model's output responses, a proxy model can be used to connect (or correlate) the input parameters and model's output responses to reduce the complexity of the procedure.

However, conventional proxy models have not been used to replace RTM to model reactive transport processes. RTM techniques are usually done using numerical programs based on the first principle of physical processes. For example, in each model, numerical simulations can be used to solve complex nonlinear partial differential algebraic equations through coupled transport engine and geochemical operators. The relationship between final simulated reactive products and the input parameters is non-linear and complex. In addition, the calculation for complex chemical reactions in typical available programs is an iterative process, where each iteration is, in general, computationally intensive.

In some implementations, workflows of proxy modeling can include the following. After a diagenetic reactive transport model and the numerical model of the RTM are set, target analysis input parameters and RTM output variables are defined. One base case of the RTM is selected and set up for experiment design. Experimental designs are run, and neural networks are trained. Predictions can then be made using the proxy model.

In conventional systems, multiple RTM simulations are usually required for input parameter sensitivity analysis and model calibration. Traditionally, this work is usually done manually. First, a modeler manually sets up input parameter files for all the experiments. Then, simulations are run manually one-by-one (or in parallel). Next, the modeler identifies relationships between the input parameters and RTM responses based on the modeler's experience and observations. The modeler can decide to change some input parameters and re-run the RTM. These steps are manually iterated until an analysis target is met. During the entire process, the modeler needs to wait while the models are running. This makes the entire process time-consuming, tedious, and mistake-prone. Therefore, it is desired to develop a computational cheap modeling method (for example, a proxy model) with a sufficient accuracy (for example, within a predefined accuracy threshold) in an automated fashion to assist in reactive transport studies.

iTOUGH2™, a computer program that provides inverse modeling capabilities, was developed by Lawrence Berkeley National Laboratory. This program can provide predictive modeling for a single forward simulation, parameter estimation, uncertainty estimation, and predication functionalities. iTOUGH2™ uses an objective function minimization algorithm to calibrate a model against observed data. The program also uses includes an objective function (to calculate a difference between model results and observed data) and a minimization algorithm (to improve the match repetitively). Although the program was originally developed for transport models without reactions, iTOUGH2™ integrated with a PEST (Parameter ESTimation) protocol has been used for geochemical parameter estimation for RTM. The PEST protocol defines the link between iTOUGH2™ and the input and output files of RTM. Proxy modeling workflow and software for RTM in this disclosure is developed particularly for automated sensitivity analysis and model calibration for RTM. The program has batch model running capabilities to generate sufficient training samples for analysis. Proxy modeling uses neural network algorithms instead of traditional objective function minimization approach.

In some implementations, the entire RTM can be considered a black box. The input to the black box can be the selected input parameters for the numerical reactive transport model. For example, the input parameters can initially be permeability, fluid injection rate, and the reactive surface area (RSA). The output from the black box can then be the final target observations of the reactive transport processes. The final target observations can include, for example, spatially distributed permeability, porosity, mineral volume fractions, and solution concentrations. The input parameters and output observations can be connected directly through a neural network.

In some implementations, the neural network in the proxy model can be trained through multiple pre-simulated cases. This approach can decrease the intensive computation burden before subsequent results analysis. In addition, parallel computation can be used to further relieve the computation burden.

Automated execution of RTM cases can include, for example, automatic picking of the observational data from the training models and machine learning model training from the collected simulated RTM results. In some implementations, procedures that perform automated execution can include following steps.

A base case scenario for reactive transport simulation can be set up. The format of input parameter files can be used as a template for automatic generating parameter files for subsequent batch runs.

An initial experimental design can be constructed using Latin hyper-cube sampling (LHS) design. The LHS design can be transferred to a physical value which includes meaningful values in hydrological and geological sense.

Initial experimental design cases can be run, for example, performed using a batch model. The results can be used as training data for neural network construction. The batch model can be run automatically in a parallel fashion, which can save labor and improve work efficiency.

Specific RTM observations can be picked from the results. Nested data architecture can be determined from the observations.

An input data tensor architecture can be constructed based on the geological model. For the 1D model, the geometry distance to the injection spot can be used directly. For 2D and 3D models, a random sample scheme can be used.

The neural network architecture can be constructed based on the input data tensor and data structure of the observations. The neural network proxy model can be trained based on the input and output of the reactive transport models. Predictions can be made with updated input parameters using the well-trained proxy model.

While the present disclosure focuses on the use of neural networks as surrogates, other techniques can be used to improve efficiency. In some implementations, deep learning neural networks or different artificial intelligence (AI) techniques can be used.

Proxy Modeling Workflow

FIG. 1 is a diagram of an example of a workflow 100 for proxy modeling, according to some implementations of the present disclosure. The workflow includes three major modules: a reactive transport base case design module 102, a training cases simulation module 104, and a machine learning based proxy model construction module 106.

The reactive transport base case design module 102 can provide functions 108 that include, for example, providing a geological and chemical reaction basis of the process. Input parameters to the reactive transport base case design module 102 can be analyzed, and target observation variables can be identified.

The training cases simulation module 104 can provide functions 110, for example, that provide a training data set for later proxy model building. Calculations can be intensive in this stage since central processing unit (CPU) times depend on the complexity of the designed reactive transport models. In some implementations, this stage can be run automatically with a batch computer command script developed for such purposes. This stage can provide parallel calculations of different scenarios and thus the computation efficiency can be improved.

The machine learning based proxy model construction module 106 can provide functions 112 that include, for example, training the neural network for each picked observation of the RTM results. The workflow 100 can include decision boxes 114, 116, 118, and 120 that are used to determine when different phases of the workflow 100 need to be run (or re-run). The well-trained neural network can be used in a predication module 122. The predication module 122, for example, can provide a computationally less intense mechanism than conventional CPU-intensive RTM simulators.

Convention Solutions to Intensive Computing Challenges of Reactive Transport Modeling Different approaches have been used to solve the intensive computing challenges of RTM. The approaches do not treat the entire RTM as a black box. Instead, the approaches replace the black box with a CPU-non-intensive process based on machine learning algorithms.

A first approach can include numerical methods based on a method of lines and differential algebraic equations (DAE) solvers, combined with a Newton method using a powerful sparse linear solver. In this approach, Newton-LU (lower-upper) methods can be used as external efficient libraries to solve the nonlinear partial differential algebraic equations. This approach is a CPU-intensive calculation procedure.

A second approach can include techniques for solving a local chemical equilibrium in a diluted solution from the minimization of the free Gibbs energy subject to linear constraints. In this approach, an objective function can be defined using logarithmic variables subjected to different linear constraints with reduced size. The strict convex character of the objective function can ensure that uniqueness is achieved, reducing iterative computing that is needed. However, this approach can be based on a mass balance equation and mass action laws. Solving optimization problem for this approach can be computationally intensive, given inequality constraints needed for processes in which minerals are precipitated and dissolved. For example, optimization can refer to achieving proxy modeling values that match RTM values within a predefined threshold.

A third approach includes using machine learning to reduce a chemical reaction calculation in a simulation procedure. For example, a smart chemical equilibrium method can be adopted for recognizing that the computational cost in chemical equilibrium is much more intensive than that in transport calculations. A machine learning accelerated chemical solver, for example, can replace original iterative chemical equilibrium calculations.

Reactive Transport Modeling

Process-based reactive transport modeling (RTM) integrates thermodynamic and kinetically controlled fluid-rock interactions with fluid flow through porous media in subsurface and surficial environments. Models can predict the temporal and spatial distribution of chemical reactions and the associated reaction products that occur in the modeled domain. RTM has been widely used to understand the migration and fate of: 1) contaminates in surface water and groundwater; 2) acid mine drainage and waste leachates; 3) stored industrial wastes and carbon dioxide; 4) the mobility of radionuclides; 5) the origin of the economic ore deposits; and 6) the impact of clastic and carbonate diagenesis on reservoir qualities of petroleum reservoirs, and mineral scale formation and inhibition in wellbores, geological formations and pipelines.

RTM can be implemented, for example, through numerical programs based on the first principle of physical processes. Naturally-occurring reactive transport processes can be characterized quantitatively and accurately through mathematical equations and solved through numerical programs. The techniques can include the use of various RTM computer programs. Input parameters for such computer programs typically include: 1) initial and boundary conditions and 2) thermodynamic and kinetic parameters. Initial conditions can include, for example, initial porosity and permeability; relative permeability and capillary pressure of a rock, temperature, and pressure; initial water composition and salinity; initial mineralogical composition of a rock; and gas composition and gas saturation. Boundary conditions can include, for example, fluid composition, flow rate, flow duration, and boundary types. Thermodynamic and kinetic parameters can include, for example, equilibrium constants for aqueous and mineral reactions involved and reaction rate parameters for minerals.

Figure 2A:
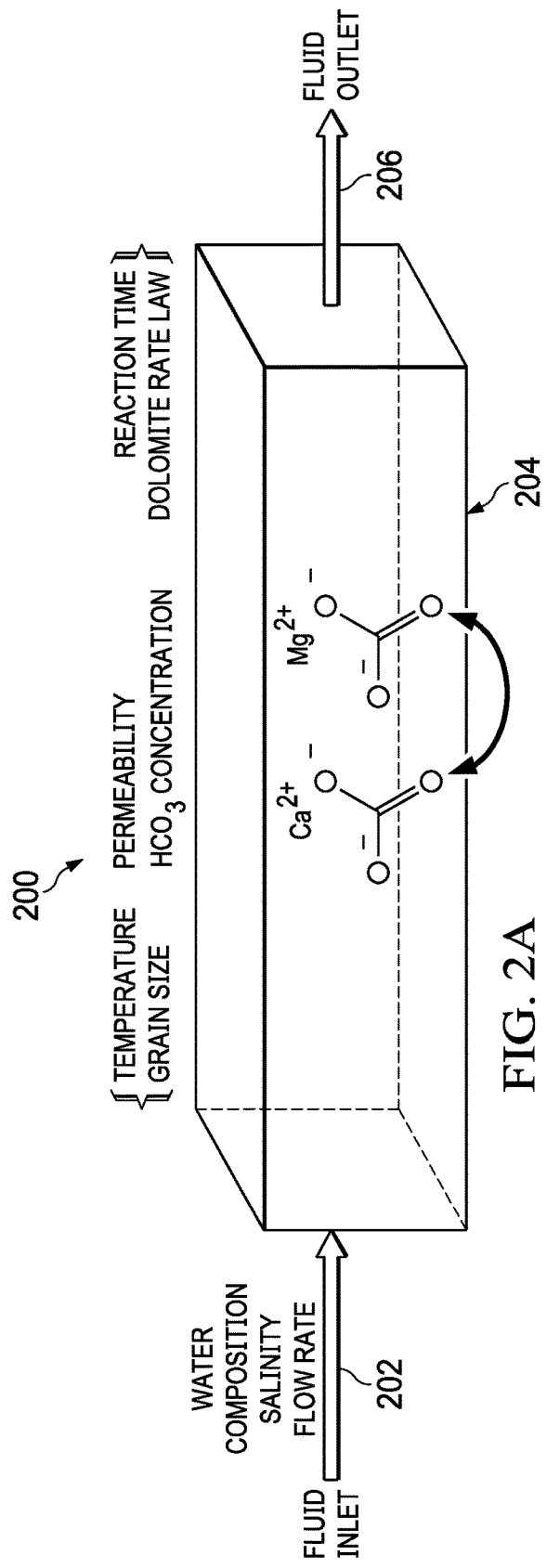
FIGS. 2A and 2B are block diagrams showing examples of a dolomitization procedure for a one-dimensional (1D) case, according to some implementations of the present disclosure.
Figure 2B:
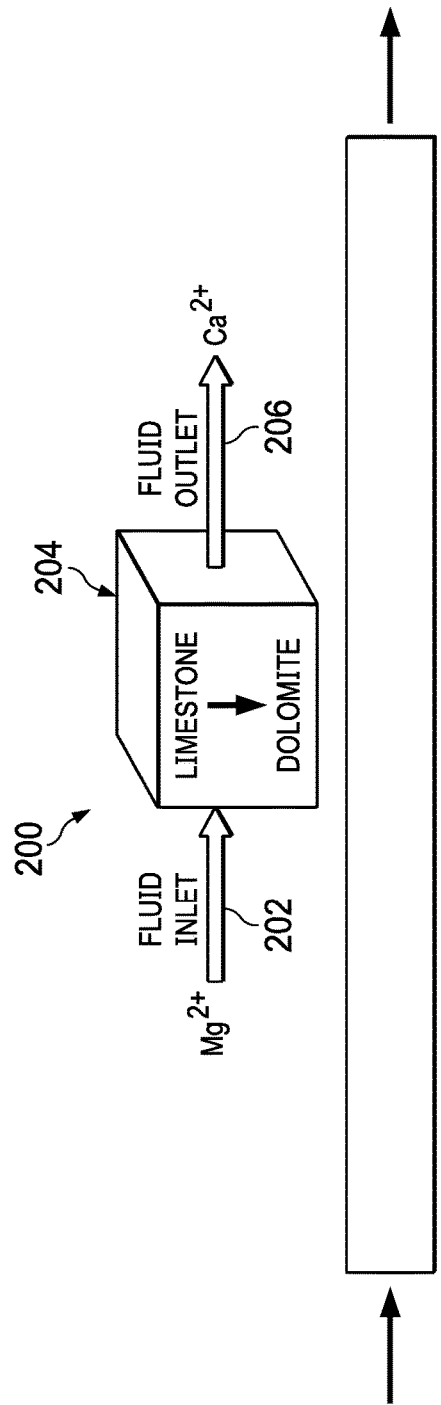

FIGS. 2A and 2B are block diagrams showing examples of a dolomitization procedure 200 for a one-dimensional (1D) case, according to some implementations of the present disclosure. In this model, an inlet fluid 202 contains magnesium ions ($Mg^{2+}$) which cause limestone to be transformed to dolomite. During dolomitization 204, the calcium ions ($Ca^{2+}$) are carried out of the model by fluid outlet 206 from the reactive procedure.

Referring to FIG. 2B, a first step in proxy modeling is to sett a diagenetic reactive transport model. For example, for a 1D dolomitization procedure, the diagenetic model can be set using the following. An input to the model can include inlet fluid flow through a porous limestone model. For example, $Mg^{2+}$ contained in the inlet fluid causes the limestone transformation to dolomite. The produced $Ca^{2+}$ is carried out of the model by the fluid from the reactive procedure. During this process, the properties of the rock particles and fluid change. The properties include, for example, porosity, permeability, the contents of dolomite and calcite, the pH and the contents of $Ca^{2+}$, $Mg^{2+}$ and $HCO_3^-$ (predicted bicarbonate ion).

Reactive Model Parameter Gridding Using Experimental Design

A representative training data set is crucial for the effective training of neural network and later proxy model accuracy. In some implementations, the representation can be achieved through reactive model parameter gridding based on experimental design. In some implementations, LHS techniques can be used to achieve a uniform representation of the entire range of input parameters.

For each reactive transport modeling, there are several recognized parameters that can be analyzed further for sedimentological or diagenetic analysis purpose. In some implementations, the parameters can be written as $x=\{x_1, x_2, \ldots, x_k\}$. Different diagenetic procedures can have a different number k of parameters x. Each parameter can denote one run for one reactive transport simulation. The use of the parameter set can produce a simulated model with a given simulation time length. In some cases, several parameter sets can be used to obtain enough proxy model training data samples to achieve successful modeling. For example, the total run number can be defined as n. The full run cases can be represented as: $X=\{x^{(1)}, x^{(2)}, \ldots, x^{(n)}\}$.

For each parameter $x_i$, a maximum value and a minimum value exist. The values can be defined as $L^i_{min}$ and $L^i_{max}$, for example. If a uniformly designed value for one input parameter is assumed to be $u_1$, then the actual sedimentological or hydrological value for the input can be calculated as $x_i = L^i_{min} + (L^i_{max} - L^i_{min}) \cdot u_i$.

Based on the RTM parameter file template, a full set of parameter files can be generated using computer applications developed for the present disclosure. The developed computer applications can be run automatically through a batch script in a parallel fashion for computational efficiency.

Neural Network Training Data Architecture

The neural network training data architecture refers to the data that carries the input and output information for training and prediction using the neural network. In some implementations, the data architecture can include three general parts. A first part can include the values of each chosen input parameter. A second part can include the spatial locations of the geological cells. A third part can include the observed values at those geological cells at different times.

Picked Reactive Process Input Parameters

For each reactive transport process, a researcher can recognize certain critical parameters based on the practical requirements or diagenetic processes. FIG. 3 is a block diagram illustrating an example of a 1D dolomitization process 300 in which several parameters 302 are used, according to some implementations of the present disclosure. Sensitive parameters such as injection rate of the inflow liquid, reaction surface area, and permeability can be identified as parameters having significant effects on dolomitization. As such, the sensitive parameters can be included in the input information of the neural network.

Representative Geological Grid Spatial Locations

The reactive transport model can be defined, for example, in certain geo-spatial locations and observed with specific time steps in a numerical simulator. The reactive transport processes can occur both in spatial and temporal space. The spatial locations of model cells can be included in the input of the training dataset for proxy model construction. Taking consideration of algorithmic efficiency, including for 1D, 2D (two-dimensional), and 3D (three-dimensional) cases, different accounting schemes can be used. Time can be used as another dimension.

In some implementations, these techniques can also be extended, for example, to three spatial dimensions. Data structures and neural network structures can be adjusted accordingly. The specific data structures that are selected can be based on the use of structures that reduce computing costs.

For the 1D case, the geometry distance to the injection spot can be used directly. This can be done because the number of grid cells is acceptable considering the computational power available.

FIG. 4A is a block diagram illustrating an example of a 1D case 400, according to some implementations of the present disclosure. The case 400 uses several parameters 402 used in the 1D case. If the cell center is spatially located as $S_i$, for example, then all the centers can be added into the input information architecture, denoted as $s=\{s_1, s_2, \ldots, s_K\}$. Considering the current computing power of computers, a 1D-managable number of cells (for example, approximately 1000 cells) can be regarded as a normal case. If the number of cells number exceeds the 1D-managable number, then the cells can be simplified using a 2D or 3D methodology.

For the 2D or 3D case (or when required by a greater number of cells in the 1D case), the training data set can be extremely large if all spatial locations are used. When this occurs, random sampling techniques can be used to effectively reduce the size of the data set. In some implementations, by selecting cells that are within x and y limits of a 2D geographic space and cell definition, cells can be picked randomly to form a training data set.

Figure 4B:
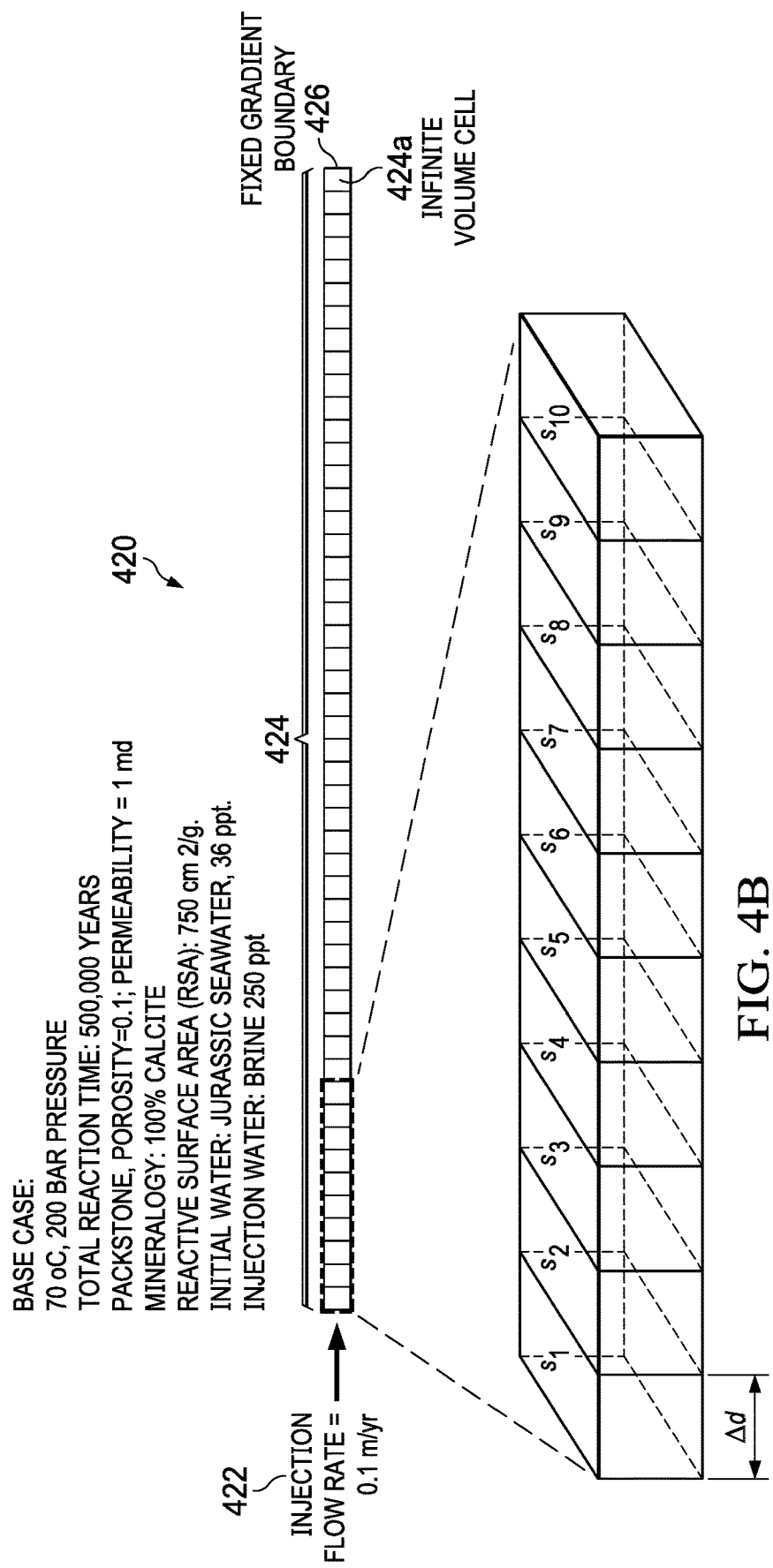
FIG. 4B is a block diagram illustrating another example of a 1D case, according to some implementations of the present disclosure.

FIG. 4B is a block diagram illustrating another example of a 1D case 420, according to some implementations of the present disclosure. As shown in FIG. 4B, an injection flow rate 422 of 0.1 m/yr (meters per year) can be present. In 1D dolomitization modeling, the limestone model can be divided, for example, into 50 grids in 1D. Fluid can be injected with a specified injection flow rate, ultimately resulting in a fixed gradient boundary 426. An end cell 424a can be set as an infinite volume cell, for example, $10^{50}$ m³ (cubic meters).

Figure 4C:
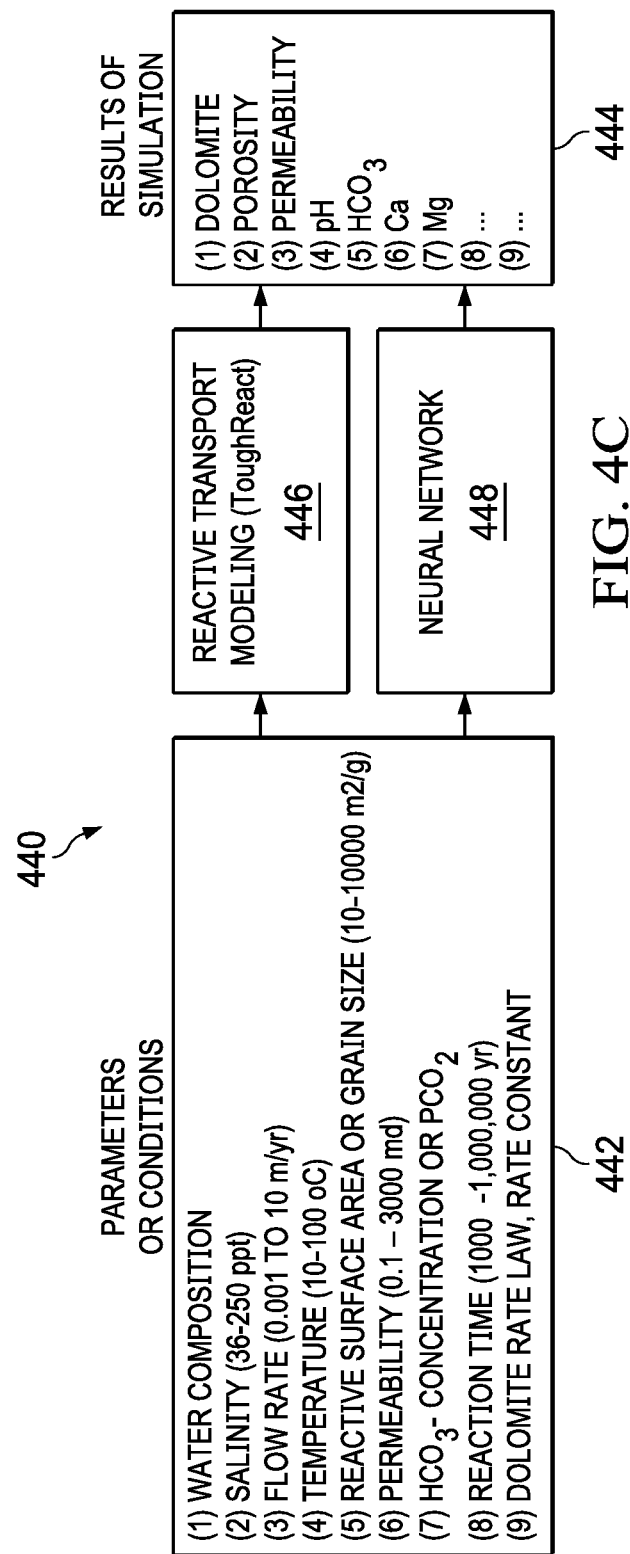
FIG. 4C is a block diagram illustrating examples of inputs and outputs of a reactive transport modeling (RTM) and a neural network, according to some implementations of the present disclosure.

FIG. 4C is a block diagram illustrating examples of inputs 442 and outputs 444 of a reactive transport modeling (RTM) 446 and a neural network 448, according to some implementations of the present disclosure. The neural network 448 can serve as a proxy for the RTM 446, for example. FIG. 4C represents the step of setting up the target analysis input parameters and RTM output variables. Target analysis input and output observation variables of the RTM can be picked for a subsequent analysis. In the 1D dolomitization example, three sensitive input parameters can be chosen from a collection of all the parameters to be used as input factors for the proxy model.

Figure 5:
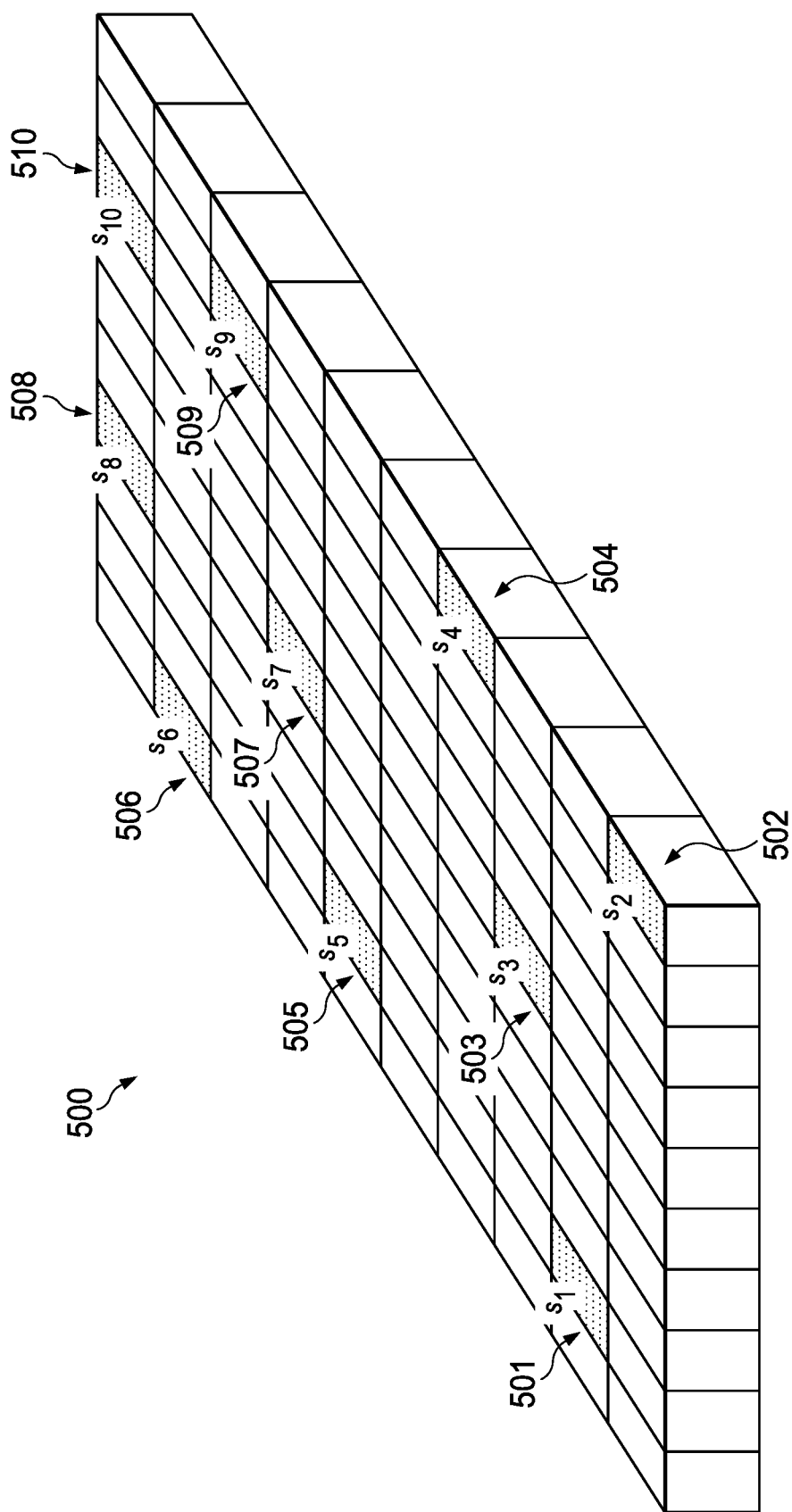
FIG. 5 is a diagram illustrating an example of a two-dimensional (2D) case, according to some implementations of the present disclosure.

FIG. 5 is a diagram illustrating an example of a two-dimensional (2D) case 500, according to some implementations of the present disclosure. The 2D case 500 includes sample spatial locations 501-510 of cell picking for parameters $s_1$ through $s_{10}$, respectively.

In some implementations, a random picking scheme a 2D case can be written in pseudo-code, for example:

```
//** Pseudo code **//
Input: x and y limit of the model, picking total number;
    Order all the cells of the 2D model;
    Randomly produce an array with size equal to picking total number;
    Order the original cells index array according to the rando array;
    From 1 to the picking number of the new-ordered cells array are the picked cells
Output: the cell index with range of picked total number;
```

Figure 6:
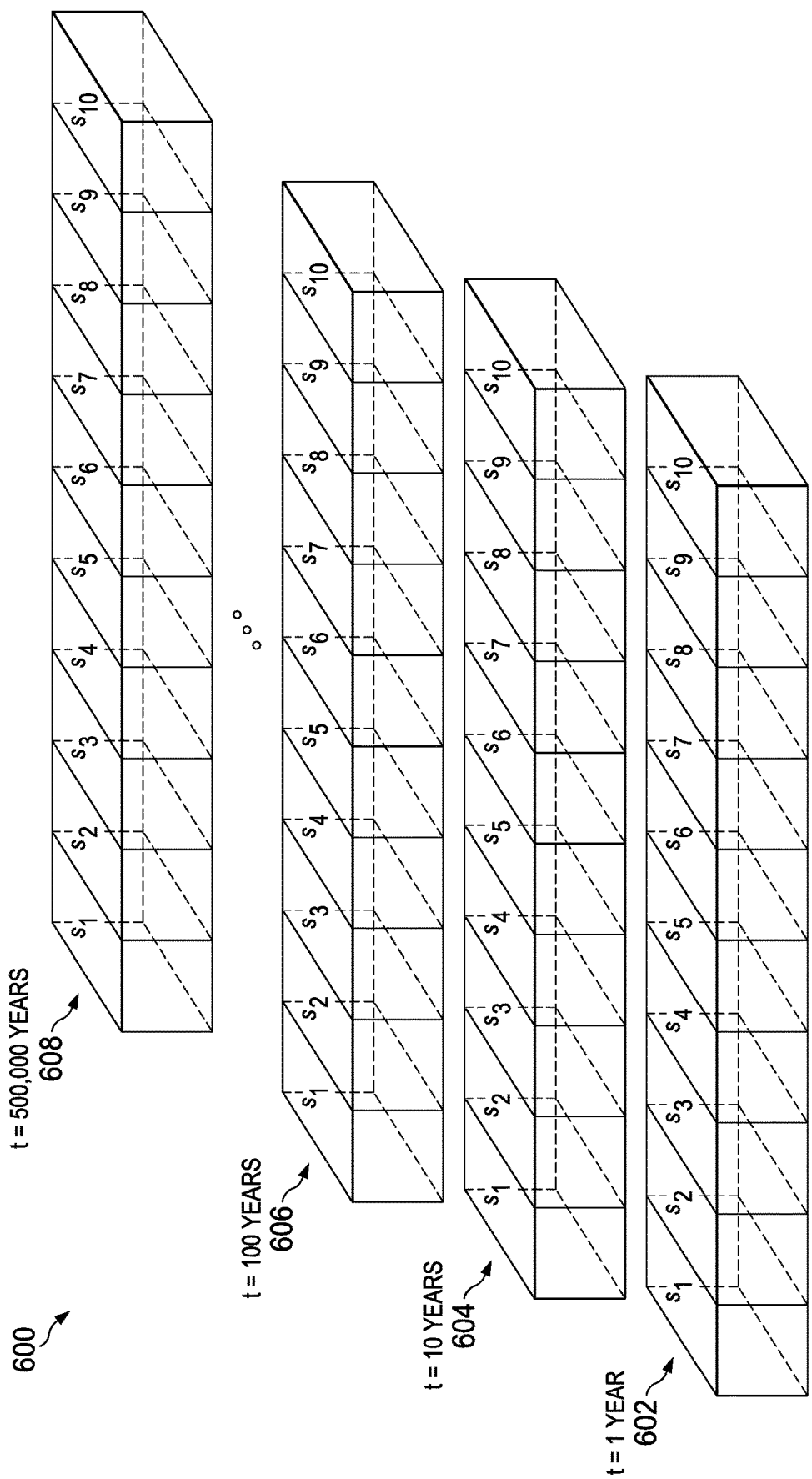
FIG. 6 is a block diagram illustrating an example of a 1D case over multiple time periods, according to some implementations of the present disclosure.

FIG. 6 is a block diagram illustrating an example of a 1D case 600 over multiple time periods, according to some implementations of the present disclosure. For example, for a reactive process simulator, different chemical processes can occur in different simulated time periods 602, 604, 606, and 608, as illustrated in the 1D case in FIG. 6. For such a temporal procedure, different reaction results can be chosen for later proxy model building given a specific observation time. Thus, in some implementations, the simulation time can also be included in the input information for the later training. In some implementations, a set of simulation times can be denoted as t
Model Observation Data After running the RTM cases, different model properties for different spatial locations at different simulation time steps can be observed. The critical properties or response variables can include spatially-distributed sediments and fluids, such as porosity, permeability, the contents of dolomite and calcite, pH, and the contents of $Ca^{2+}$, $Mg^{2+}$ and $HCO_3$. These observations are denoted as $y=\{y_1, y_2, \ldots, y_m\}$. The properties can be used as output target parameter for the training of the proxy models.
Proxy Modeling Based on Neural Network Neural networks can be one of basic machine learning techniques used to build the proxy model of RTM in the present disclosure. The neural network consists of one input layer, one output layer, and multiple hidden layers. The input layer receives the signal, and the output layer outputs the final results. The hidden layer consists of multiple parallel neurons containing the activation functions. More details of the proxy model are given in the following sections.

Figure 7:
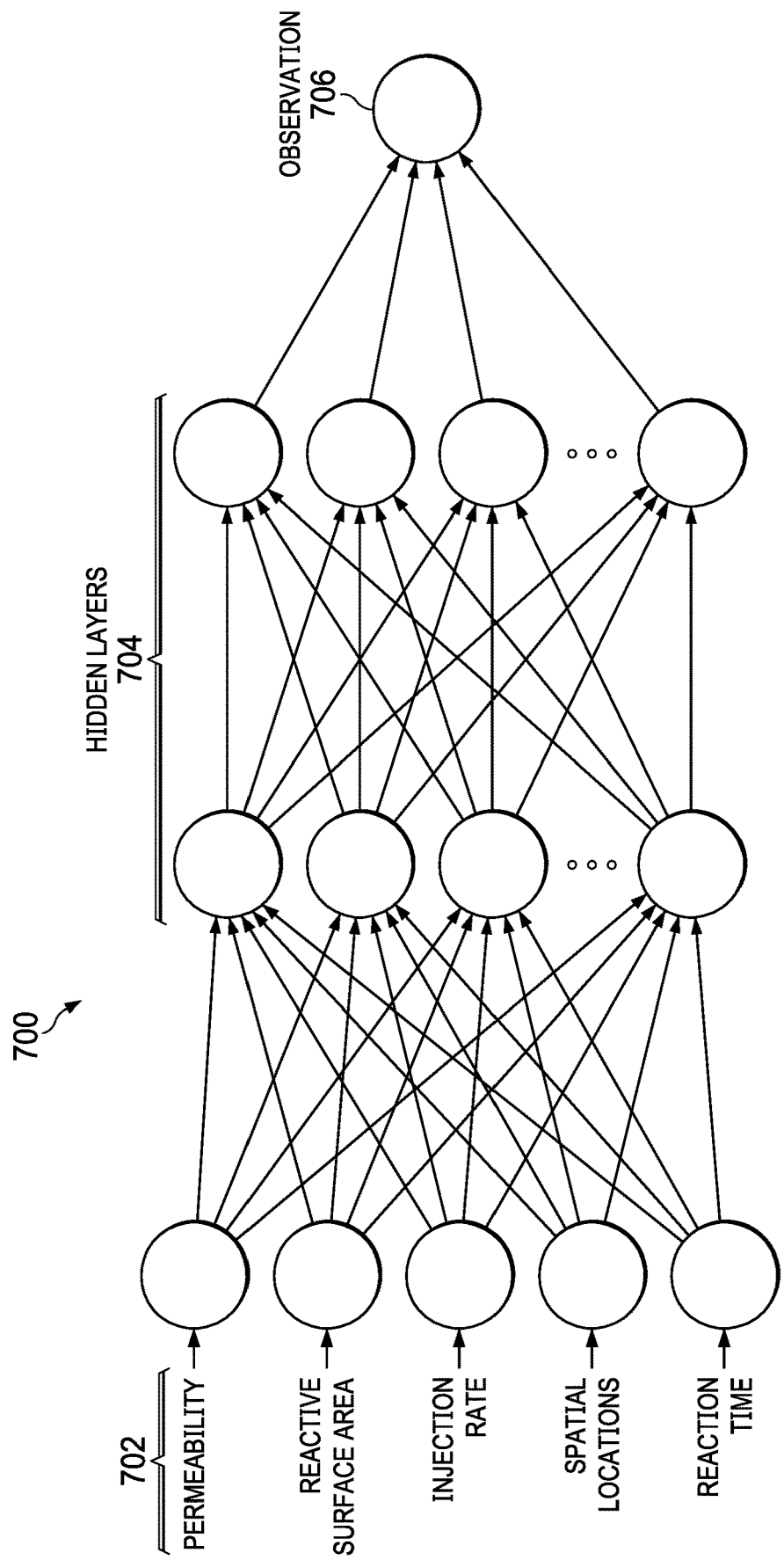
FIG. 7 is a diagram showing an example of a neural network architecture, according to some implementations of the present disclosure.

FIG. 7 is a diagram showing an example of a neural network architecture 700, according to some implementations of the present disclosure. The neural network archi-tecture 700 can be a proxy for an RTM, for example. Input signals 702 of the neural network architecture 700 can serve as input parameters of the RTM. The input signals 702 can include, for example, permeability, RSA, injection rate, spatial location, and reaction times. In the illustrated example of FIG. 7, two hidden layers 704 are chosen for the 1D dolomitization modeling. However, any appropriate neural network can be adopted for the specific proxy modeling. An observation 706 (for example, the content of dolomite) serves as the only neuron in the output layer.

The learning process of the neural network can be equivalent to the minimization of the loss function. An optimization function can be used to find the minimum of the loss function. A well-established stochastic gradient descent (for example, the Adam optimization algorithm) can be used as the optimization function. A backpropagation (BP) technique can be used in the training process to calculate gradients from the output.

Training cases can be divided randomly into training, validation, and testing subsets. The training subset can be used to train the neural network. The validation subset can be used to monitor the training process. Training can be terminated, for example, if the loss of the validation is not improving. Alternatively, the user can terminate the training processing manually. The testing subset can include random blind data and can be used to test the trained neural network. A well-trained neural network model can be used to fit the training, validation and testing subsets.
Proxy Model Notation In some implementations, the neural network can be chosen as the proxy model engine. An RTM process can be donated as f(•) and the proxy model can be donated as f̂(•). The proxy model can be considered to be a "cheap-to-evaluate" because the computation time it requires is less than an RTM computation time. The procedure f(•) can require a k-vector of design variable x. Based on the available results of RTM runs, some observations can be obtained at the given location s and given reaction time t, which can be written as $\{x^{(i)},s,t \rightarrow y^{(i)}=f(x^{(i)},s,t), i=1, 2, \ldots, n\}$. The set of designs can be denoted as $X=\{x^{(1)}, x^{(2)}, \ldots, x^{(n)}, s,t\}$. The observations from these designs can be denoted as $Y=\{y^{(1)}, y^{(1)}, \ldots, y^{(n)}\}$.

In proxy modeling based on neural networks, the design variable x, the spatial location s, and the reaction time t can serve as the input signals of the network, such as shown in FIG. 6. Thus, a target of proxy modeling can be to find an appropriate neural network which can connect X and Y together, which can be noted as Y=f̂(X). The model f̂(•) can approximate the original f(•) and serve as a relatively inexpensive (for example, computationally) performance prediction for any updated reactive process parameters.
Nested Neural Network Training Strategy Observations resulting from RTM output can be related. For example, when the observations include changes in dolomite content, variations in porosity can also be observed. In some cases, the observations may not be surrogated all at once, for example, with the same priority or timing. In some implementations, the observations can be made using a nested training strategy. For example, an observation can be based on a previously-made observation.

In a nested training strategy, a first step can be to pick one critical observation based on the expert's knowledge. For example, in a dolomitization process, the dolomite content will be affected by other model observations. Therefore, dolomite content can be considered a critical variable of interest. In the nested neural network training, the dolomite content can be surrogated first. After the prediction of dolomite content from the proxy model satisfies pre-determined accuracy criteria, the dolomite content from the training data set can be regarded as input training information for other observations, such as porosity and pH.

Figure 8:
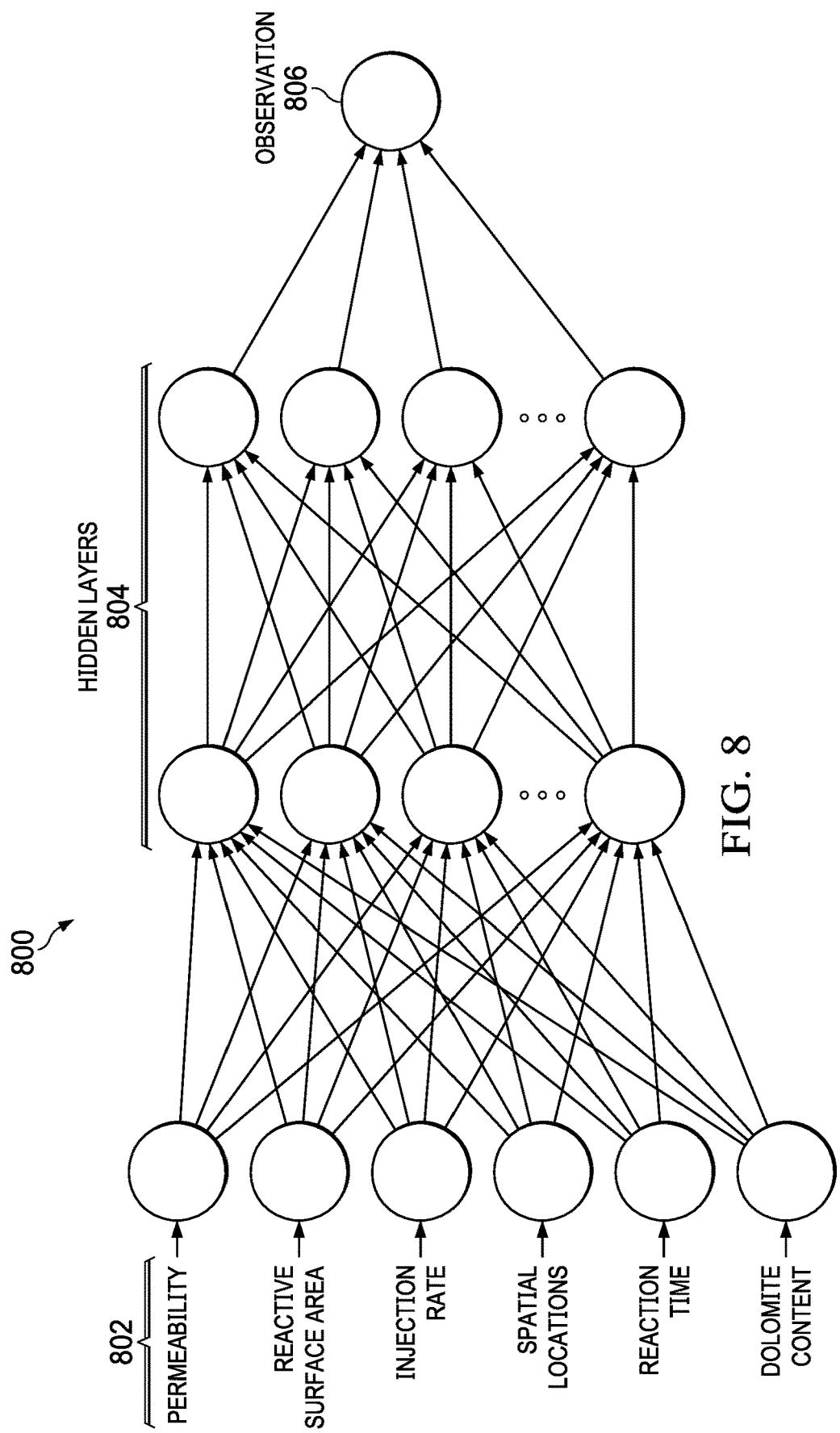
FIG. 8 is a diagram showing an example of a nested neural network architecture, according to some implementations of the present disclosure.

FIG. 8 is a diagram showing an example of a nested neural network architecture 800, according to some implementations of the present disclosure. In the nested neural network architecture 800, one more neuron (in this example, dolomite content) is added to the input signals layers represented by input signals 802. The nested neural network architecture 800 includes hidden layers 804. An observation 806 in this example, is based on dolomite content, which can be the observation 706 in the neural network architecture 700.

Nested Prediction Based on Neural Network Proxy Model

After a determination is made that the proxy model for each observation variable meets accuracy criteria, the proxy model can be used directly for making predictions. During the process of making predictions, similar nested prediction strategies can be adopted. For example, as shown in the example of FIG. 8, a critical observation variable can be predicted first. The prediction values of the critical observation variable can be used as input information for other specific observation prediction. For example, in the dolomitization process, the dolomite content can be predicted first. Then, the predicted dolomite content can be used as input information for other observation prediction.

Figure 9:
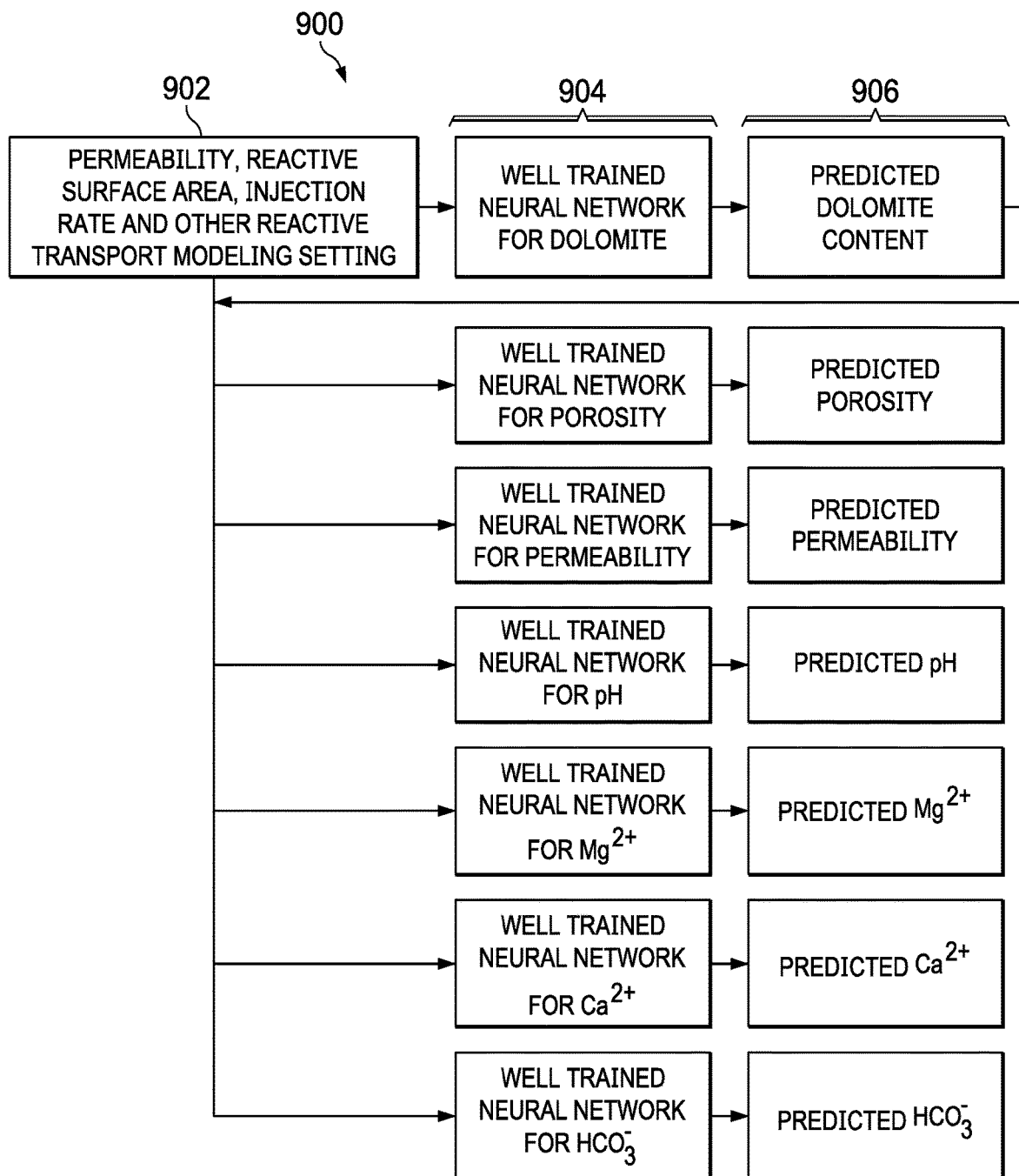
FIG. 9 is a diagram showing an example of a nested neural network architecture, according to some implementations of the present disclosure.

FIG. 9 is a diagram showing an example of a nested neural network architecture 900, according to some implementations of the present disclosure. The nested neural network architecture 900 can use input signals 902. The input signals 902 can include, for example, permeability, RSA, injection rate, and different RTM settings. The nested neural network architecture 900 includes nested neural networks 904, where each subsequent neural network is based on observations 906 determined by previous neural networks. The observations 906 can include, for example, predicted dolomite content, predicted porosity, predicted permeability, predicted pH, predicted $Mg^{2+}$, predicted $Ca^{2+}$, and predicted bicarbonate ion $HCO_3^-$.

Example Using Methodology of Present Disclosure

An example follows that is based on techniques described in the present disclosure. The example applies to a 1D dolomitization procedure, for example. In this example, initial settings of the RTM include: 1) a temperature of 70° C. (Celsius); 2) a pressure of 200 bars, 3) a total reaction time of 500,000 years; 4) rock properties (packstone, porosity=0.1, and permeability=1 millidarcy (md); 5) mineralogy (100% calcite, RSA=750 $cm^2/g$ (square centimeters per gram)); 6) initial water (Jurassic seawater with a salinity of 36 ppt (parts per thousand), and injection water: brine with a salinity of 250 ppt). The values can be included in an input parameter file that is used as a template for automatic parameter file generator. For example, the values can be used in a base case that is run before LHS design.

A physical model and dynamic set (for example, corresponding to FIG. 4B) is now given. Using the input parameters (for example, initial settings of the RTM), three key parameters (for example, permeability, RSA, and injection rate) can be selected to design different cases which will be run for subsequent proxy model training. Ranges of the variable can include: 1) injection rate of 0.001 to 10 m/yr; 2) RSA or grain size of 10 to 10,000 $m^2/g$ (square meters per gram); and 3) permeability of 0.1 to 3000 md.

Figure 10A:
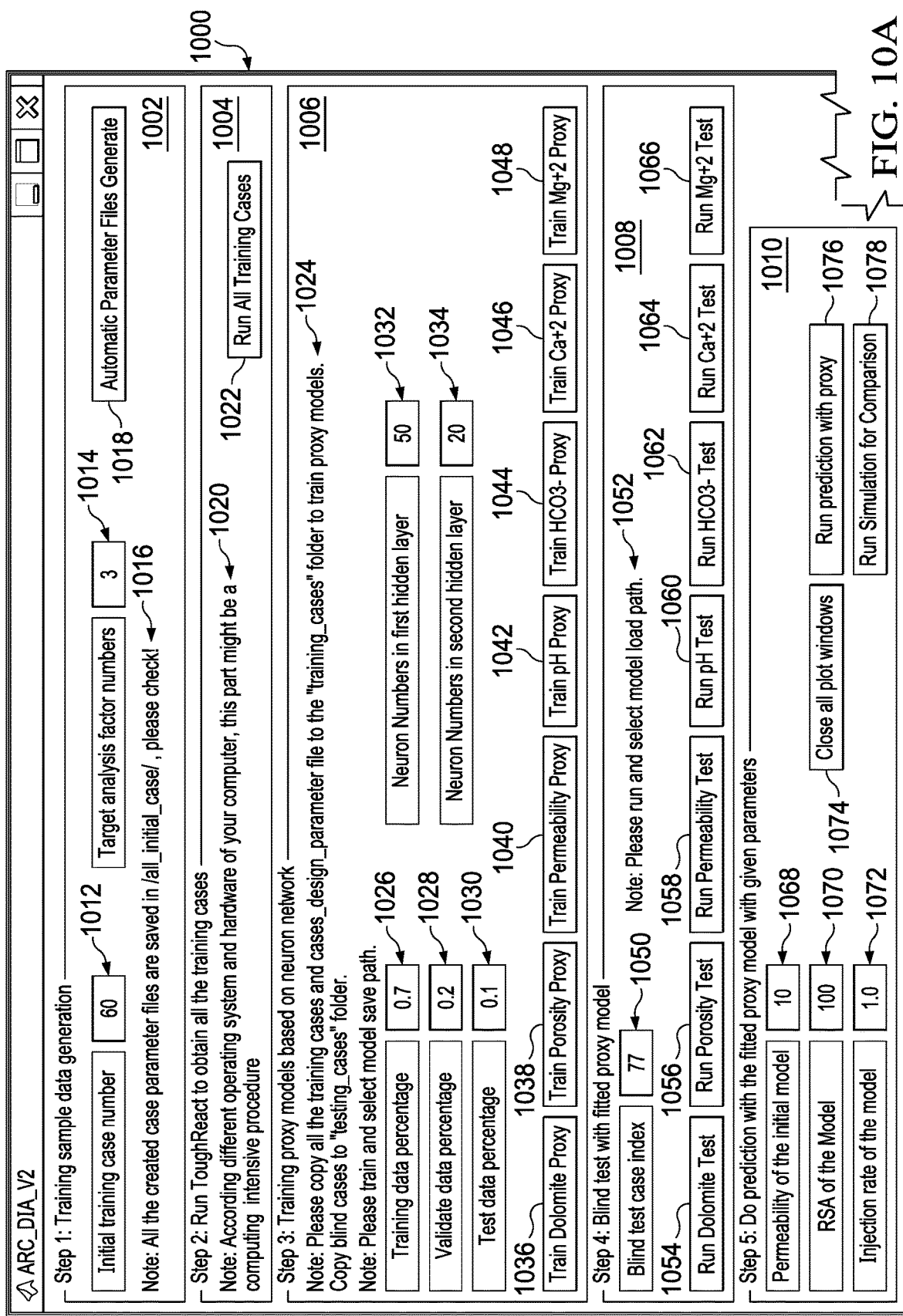
FIG. 10A is a screenshot of an example of a graphical user interface (GUI) for training and using a proxy model, according to some implementations of the present disclosure.

FIG. 10A is a screenshot of an example of a graphical user interface (GUI) 1000 for training and using a proxy model, according to some implementations of the present disclosure. The GUI 1000 can be used to automatically generate case design parameters using LHS techniques, and to automatically generate simulation parameter files (for example, ToughReact™ parameter files). The parameter files can replace target strings of designed parameters in parameter file template provided, for example, in a base case. The GUI 100 includes five sub-panels 1002, 1004, 1006, 1008, and 1010 that are configured to accept user input for five steps of training and executing the proxy model.

Using a training sample data generation sub-panel 1002, a user can use the GUI 1000 for case design, including to define key parameters and a number of LHS designs. For example, field 1012 is a text box that is configured to receive the user's input on the number of the initial training cases (for example, numbering in the hundreds). Field 1014 is a text box that is configured to receive the user's input on the number of target analysis factors. In some implementations, three key parameters can be selected to design different cases that include, for example, permeability, RSA, and injection rate. Note 1016 is a static text box frame that is configured to a display a reminder (or tip) to the user, for example, to identify a location of output files.

In some implementations, the range for each key factor can be displayed in the GUI. To make changes to the ranges, the user can locate a table (for example, "initial_range.xlsx") that is separate from the GUI and lists range values. The table can be clicked for editing, resulting in a separate interface being displayed in which the user can define ranges of values of the target analysis factors.

Once the training sample data is defined, the user can click on a generate control 1018 (for example, an "Automatic Parameter Files Generate" push button) to initiate subsequent processing. Clicking on the generate control 1018 runs a program, for example, that automatically generates a file (for example, a spreadsheet file) containing the key parameters set in each training case. In some implementations, the file that is created can be a comma-separated file, for example, "cases designparameters.csv." The file can be copied to various folders as needed for subsequent processing. The scope and results of the processing will depend on values of the inputs. The inputs include field 1012 (for example, 60), controlling how many parameter files will be generated, and field 1014 (for example, 3), controlling how many parameters in each file are designed.

Sub-panel 1004 includes a field 1020 (for example, a static text box frame) that is configured to provide a reminder or tip to the user regarding execution of the sub-panel 1004. Control 1022 (for example, a push button) is configured, when clicked, to automatically launch execution of background programs for each training case. Steps included in the execution can include, for example, automatically running the simulation with the design cases to generate case data. Each case can be run manually, or automatically in parallel with other cases. Execution of background programs for each training case can produce a set of simulated models (for example, ToughReact™ models). The number of models that are created can depend on the value of field 1012.

FIG. 10B is a screenshot of an example of a user interface (UI) 1080 that displays the status of each training case, according to some implementations of the present disclosure. For example, individual lines of information in the UI 1080 can be updated, allowing the user to track the progress of execution of the training cases, including providing statistics of background diagenetic simulation running status. A first column 1082 identifies the current simulation steps. A second column 1084 identifies the total steps for each training case of the diagenetic simulation. A third column 1086 is a proportion of run steps by total steps. A fourth column 1088 is configured to provide status. Statuses can include, for example: 1) "Not run yet" 2) "Finished running" 3) "Running is in bad setting, should be stopped" and 4) "Running is in good setting and not finished yet." FIG. 10C is a screenshot of an example of the UI 1080 that displays the status of each training case, according to some implementations of the present disclosure.

In some implementations, optimum results for creating test data can include the following. 100 to 200 LHS design cases can be generated. The cases can be run with an automatic forward running engine. The user can suspend the program (for example, by pressing Ctrl+C). Then the user can re-start the program by activating the control 1022. If the user decides that a sufficient number of "Finished running" cases exist for training, then the user can stop the program (for example, by pressing Ctrl+C). A sufficient number can correspond to a case in which the user believes that acceptable results can be achieved from the cases already run. However, if the user decides that not enough "Finished running" cases exist, then the user can let the program continue to run. If a specific case is determined not to be converging using the parameter file settings, then the program can stop the simulation automatically.

Figure 11A:
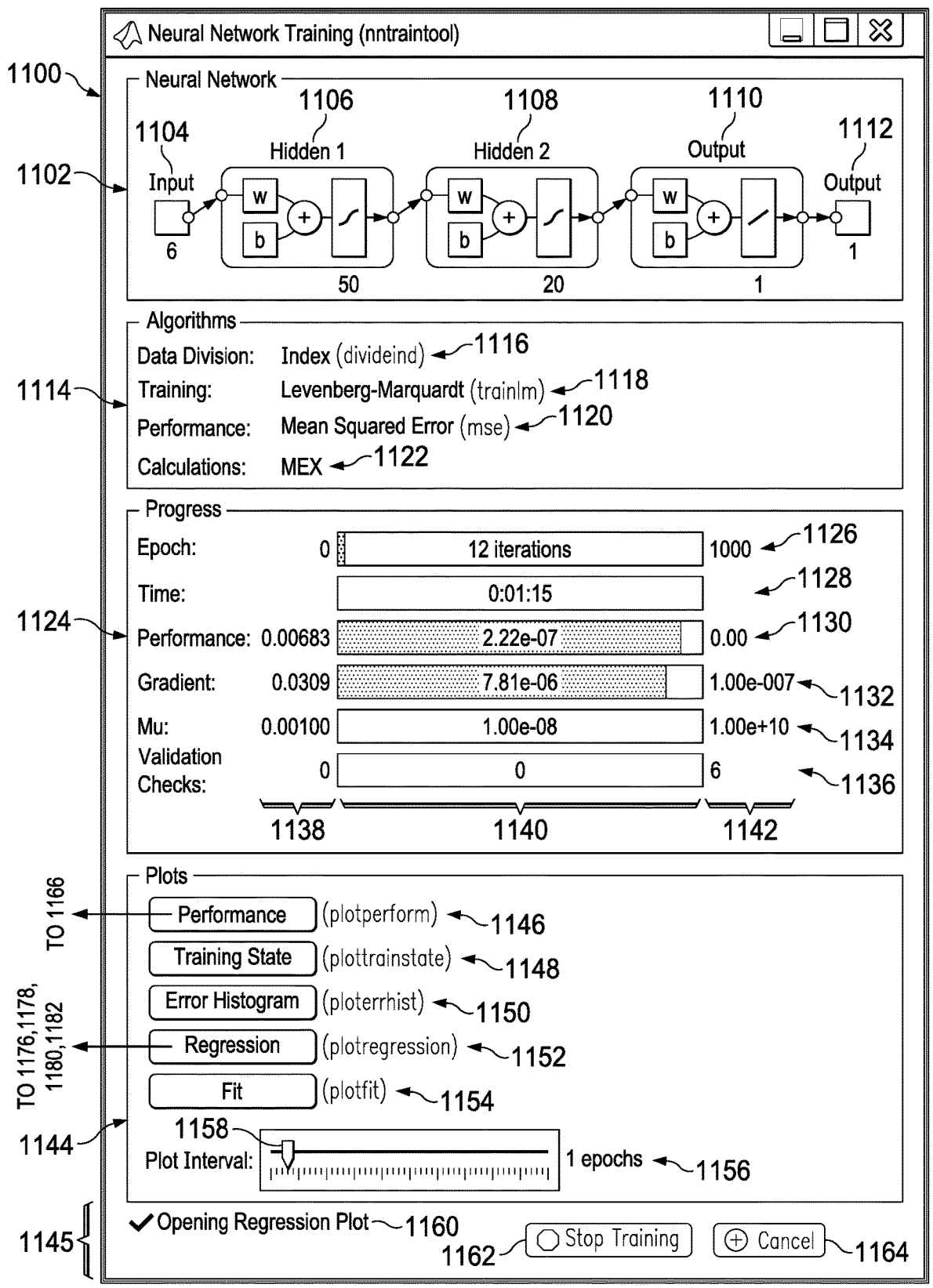
FIGS. 11A-11C are screenshots collectively showing examples of components of a neuron network toolbox UI from a multi-paradigm numerical computing environment, according to some implementations of the present disclosure.
Figure 11B:
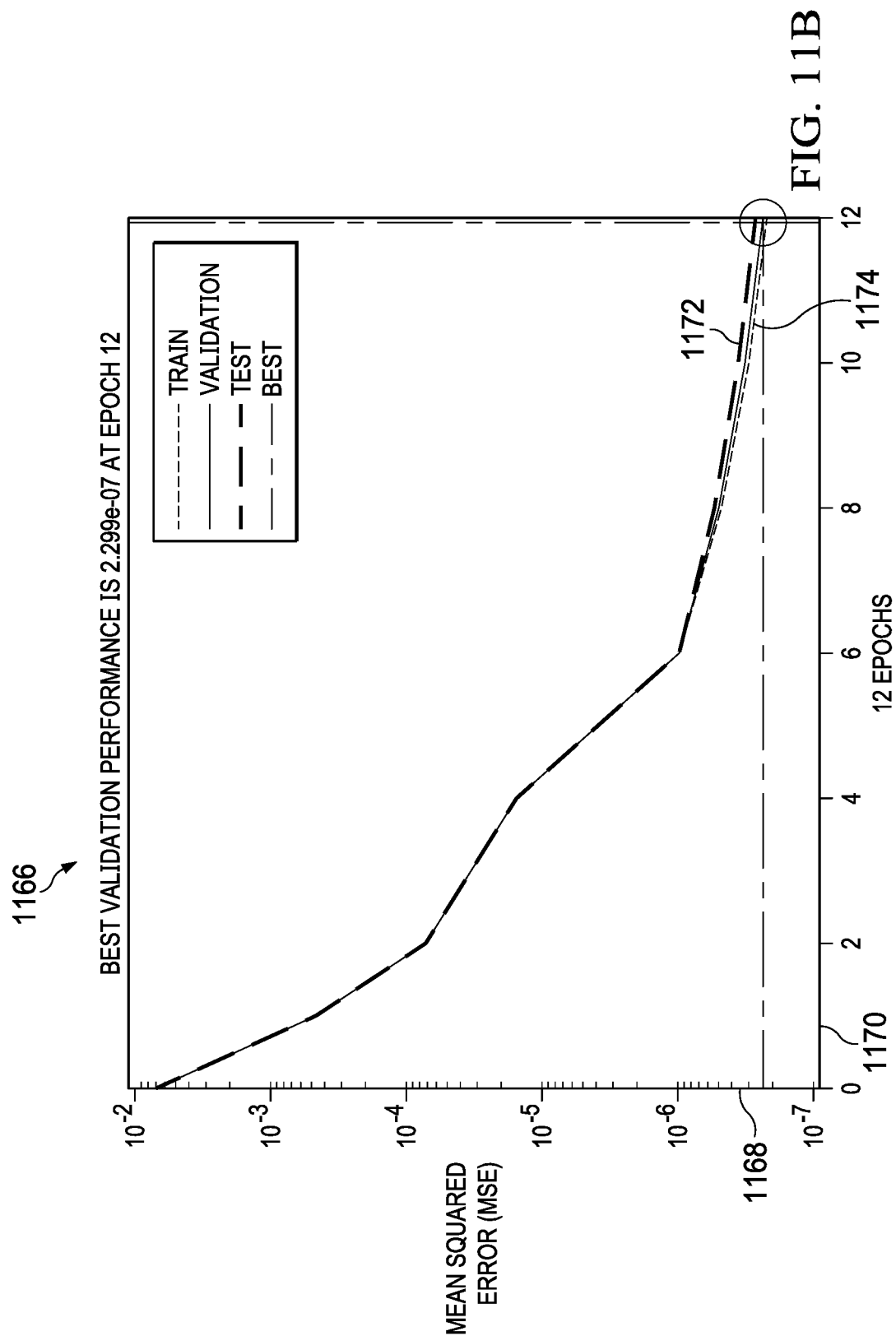
Figure 11C:
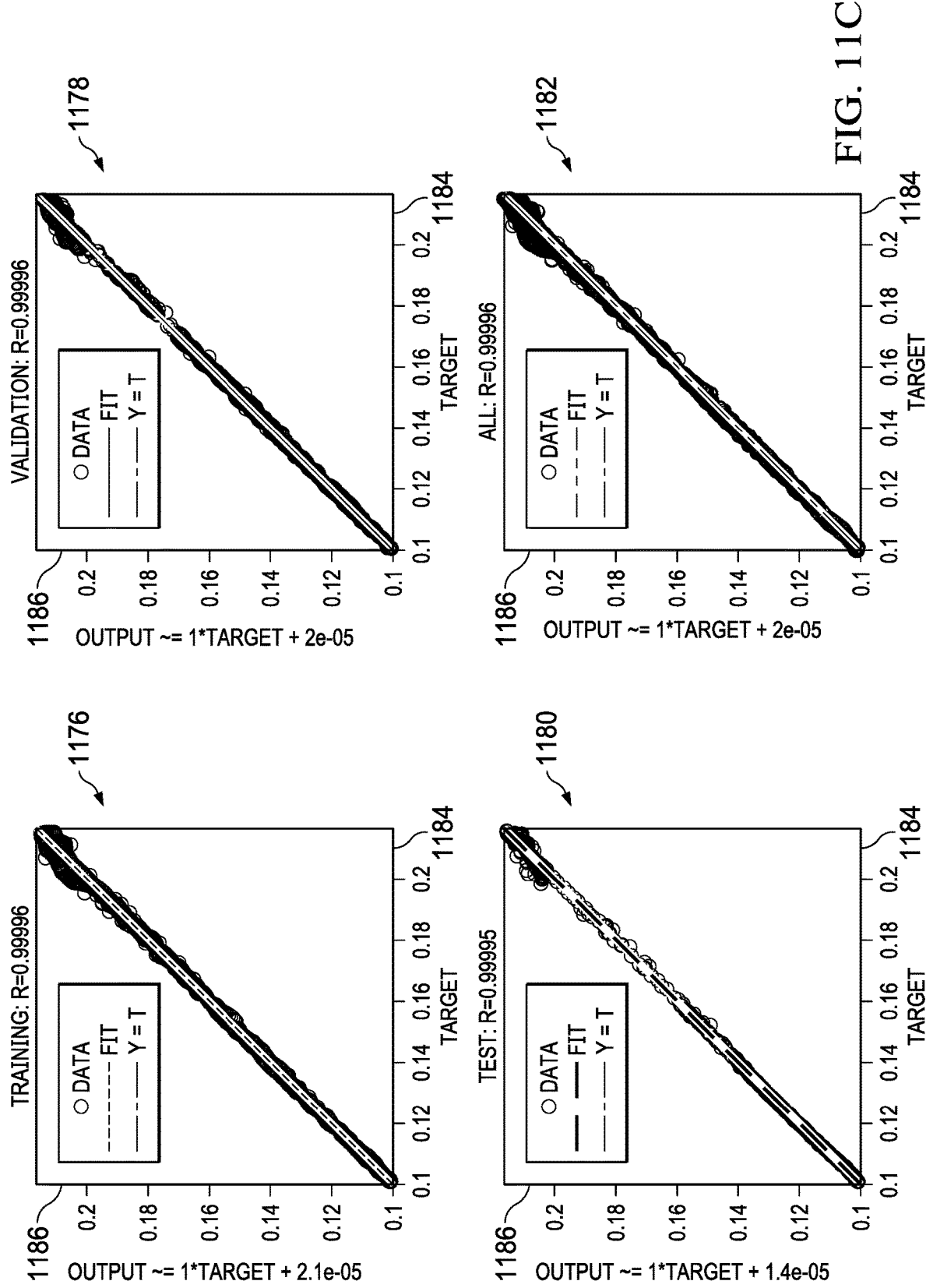

Referring again to FIG. 10A, in sub-panel 1006, a static text box frame 1024 can display a reminder (or tip) to the user regarding details of executing the sub-panel 1006. Text box 1026 can receive the user's input on a training data percentage. Text box 1028 can receive the user's input on a validate data percentage. Text box 1030 can receive the user's input on a test data percentage. Text box 1032 can receive the user's input for a neuron number in a first hidden layer. Text box 1034 can receive the user's input for a neuron number in a second hidden layer. Controls (for example, push buttons) 1036, 1038, 1040, 1042, 1044, 1046, and 1048 can be used to initiate training on respective proxies, resulting in the presentation of a UI described with reference to FIGS. 11A-11C. Values provided for text boxes 1026, 1028, 1030, 1032, and 1034 can be used with functions available in the multi-paradigm numerical computing environment (for example MATLAB™) to produce neural networks as shown in FIGS. 11A-11C. During training, a neural network toolbox available in the multi-paradigm numerical computing environment can be used. A user can terminate the training based on user observations and understanding of statistics and information shown in user interfaces corresponding to FIGS. 11B and 11C.

In sub-panel 1008, a text box 1050 can receive the user's input on the blind test case index. A static text box frame 1052 can display a reminder (or tip) to the user regarding details of executing the sub-panel 1008. Controls 1054, 1056, 1058, 1060, 1062, 1064, and 1066 (for example, push buttons) can be used to initiate blind testing of the models for the respective proxies and result in displaying the UI elements shown in FIGS. 12A-12F.

In sub-panel 1010, a text box 1068 is configured to receive user's input on "permeability" of the model. A text box 1070 is configured to receive the user's input on "RSA" of the model. A text box 1072 is configured to receive the user's input on the "injection rate" of the model. Clicking on a control 1074 will close all the displays. A control 1076 is configured to run the proxy model to make a prediction. For example, well-trained models can be used to perform predictions on additional designed cases with different parameters. FIG. 10E is a diagram showing examples of outputs 1096 that are created when the proxy model is run to make a prediction. Some of the outputs 1096 can be used to display graphical representations, for example, as shown in FIGS. 12A-12F. A control 1078 is configured to run the simulation (for example, ToughReact™) for comparison. Running the simulation produces the UI described with reference to FIG. 12F.

FIG. 10D is a diagram showing examples of source code components 1090 used for proxy RTM, according to some implementations of the present disclosure. For example, the source code components 1090 include demo data sets 1091, a main program file 1092, subroutines 1093, and trained proxy models 1094 that result from training. FIG. 10E is a diagram showing examples of files 1096 used for proxy RTM, according to some implementations of the present disclosure.

FIGS. 11A-11C are screenshots collectively showing examples of components of a neuron network toolbox UI 1100 from a multi-paradigm numerical computing environment, according to some implementations of the present disclosure. The neuron network toolbox UI 1100 can be a standard, default tool provided by the multi-paradigm numerical computing environment that also supports a scripting language (for example MATLAB™). The neuron network toolbox UI 1100 includes a neural network sub-panel 1102, an algorithms sub-panel 1114, a progress sub-panel 1124, a plots sub-panel 1144, and controls 1145. The neural network sub-panel 1102 includes a graph showing inputs 1104, intermediate neural networks 1106, 1108, and 1110, and an output 1112. The algorithms sub-panel 1114 includes algorithm parameters 1116, 1118, 1120, and 1122. The progress sub-panel 1124 includes parameters 1126, 1128, 1130, 1132, 1134, and 1136 which are organized by columns 1138, 1140, and 1142. The plots sub-panel 1144 includes parameters 1146, 1148, 1150, 1152, 1154, 1156, and 1158. Controls 1145 include controls 1160, 1162, and 1164.

Plots 1166, 1176, 1178, 1180, and 1182 result from selections made from the neuron network toolbox UI 1100. The plot 1166 includes lines 1172 and 1174 plotted relative to axes 1168 and 1170. The plots 1176, 1178, 1180, and 1182 include data plotted relative to correlation axes 1184 and 1186.

Figure 12A:
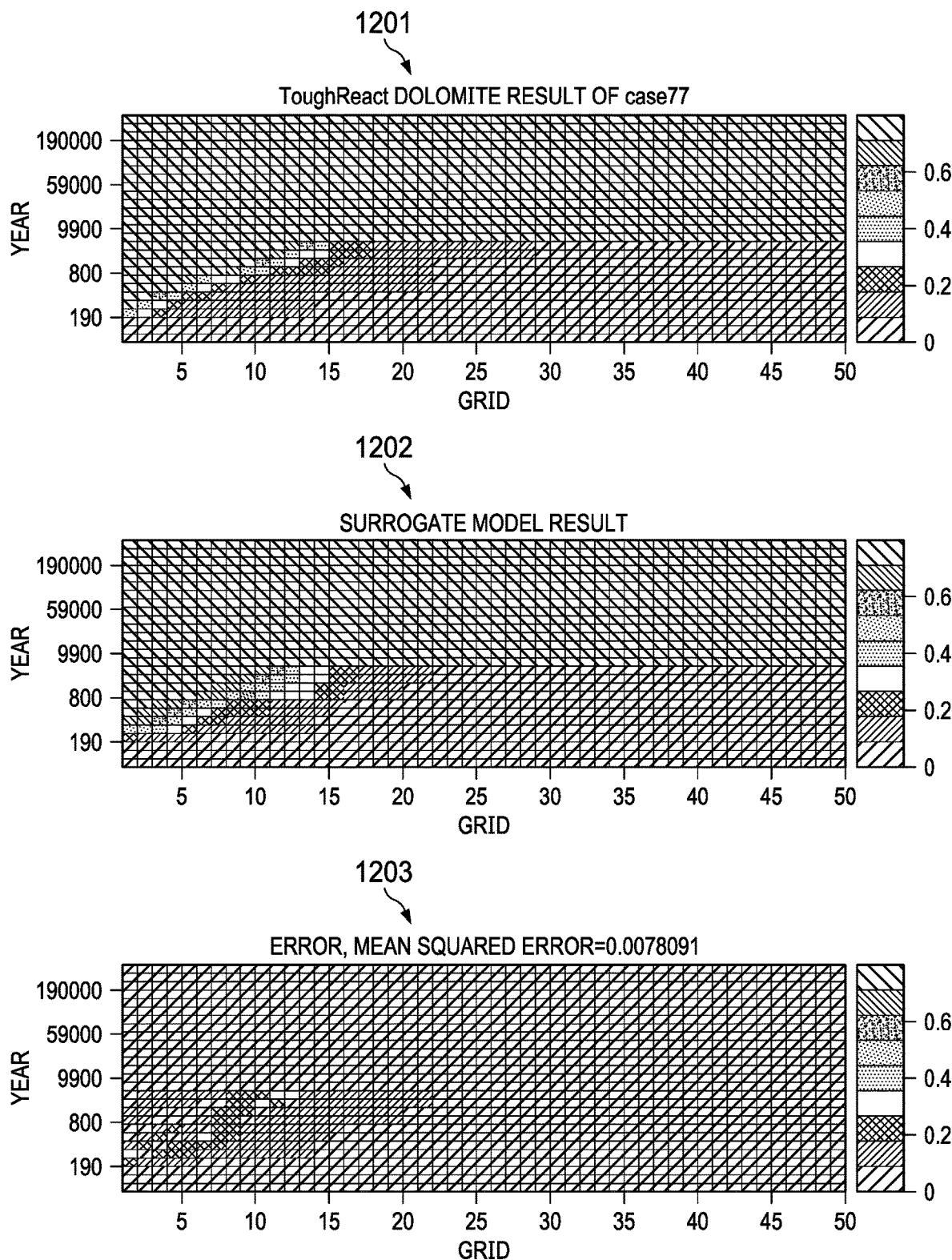
FIGS. 12A-12F are examples of UI elements that are produced during execution of the UI, according to some implementations of the present disclosure.
Figure 12B:
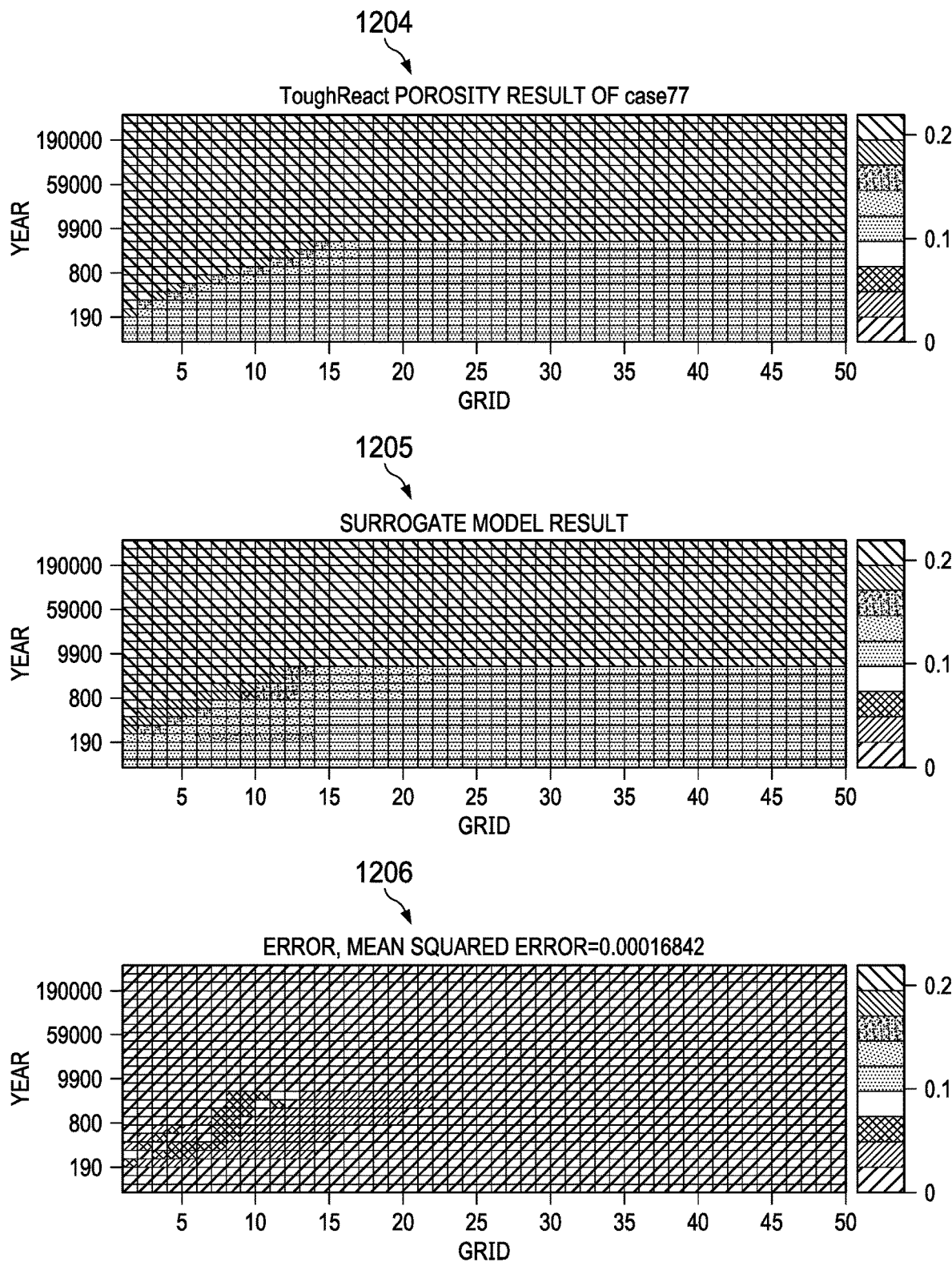
Figure 12C:
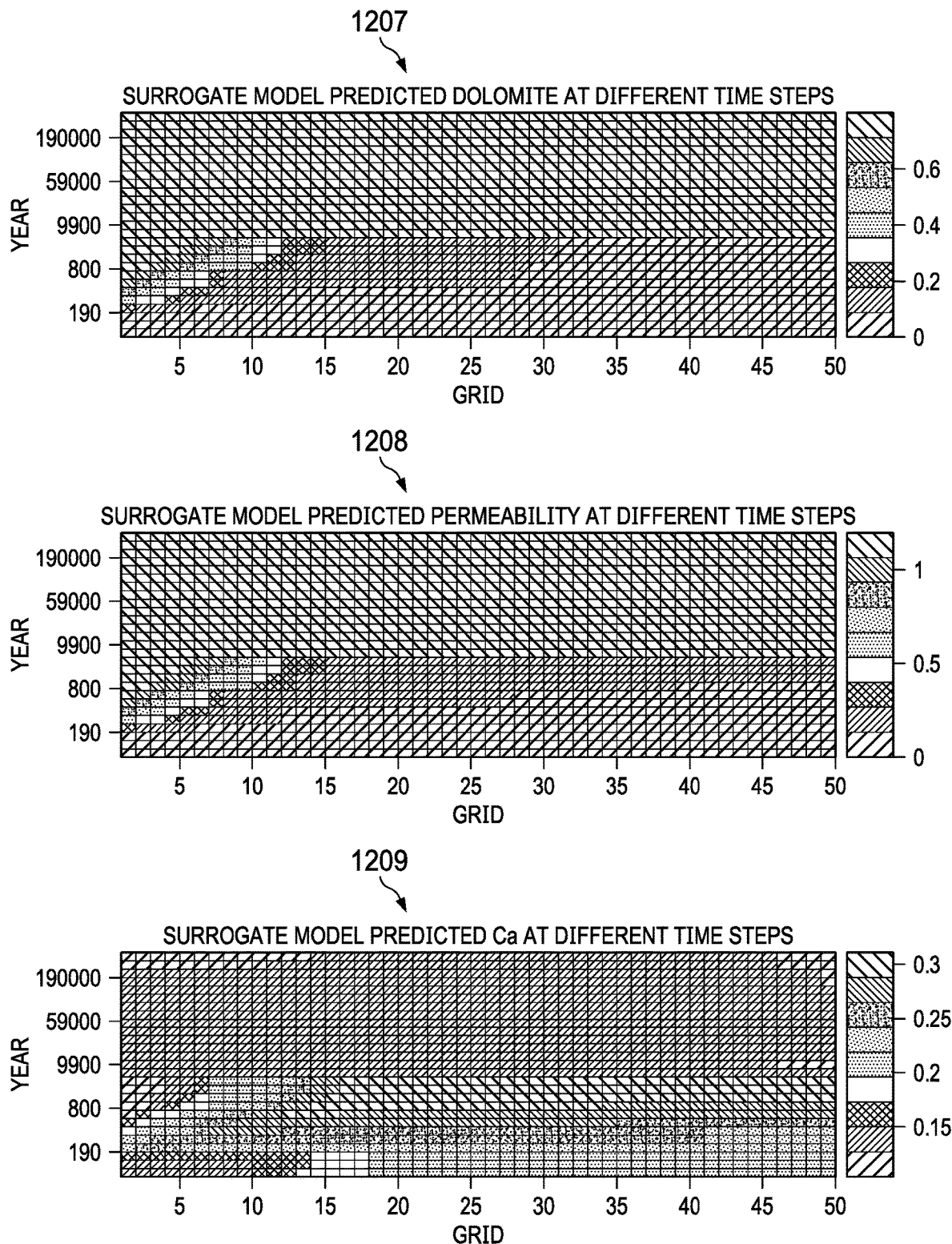
Figure 12D:
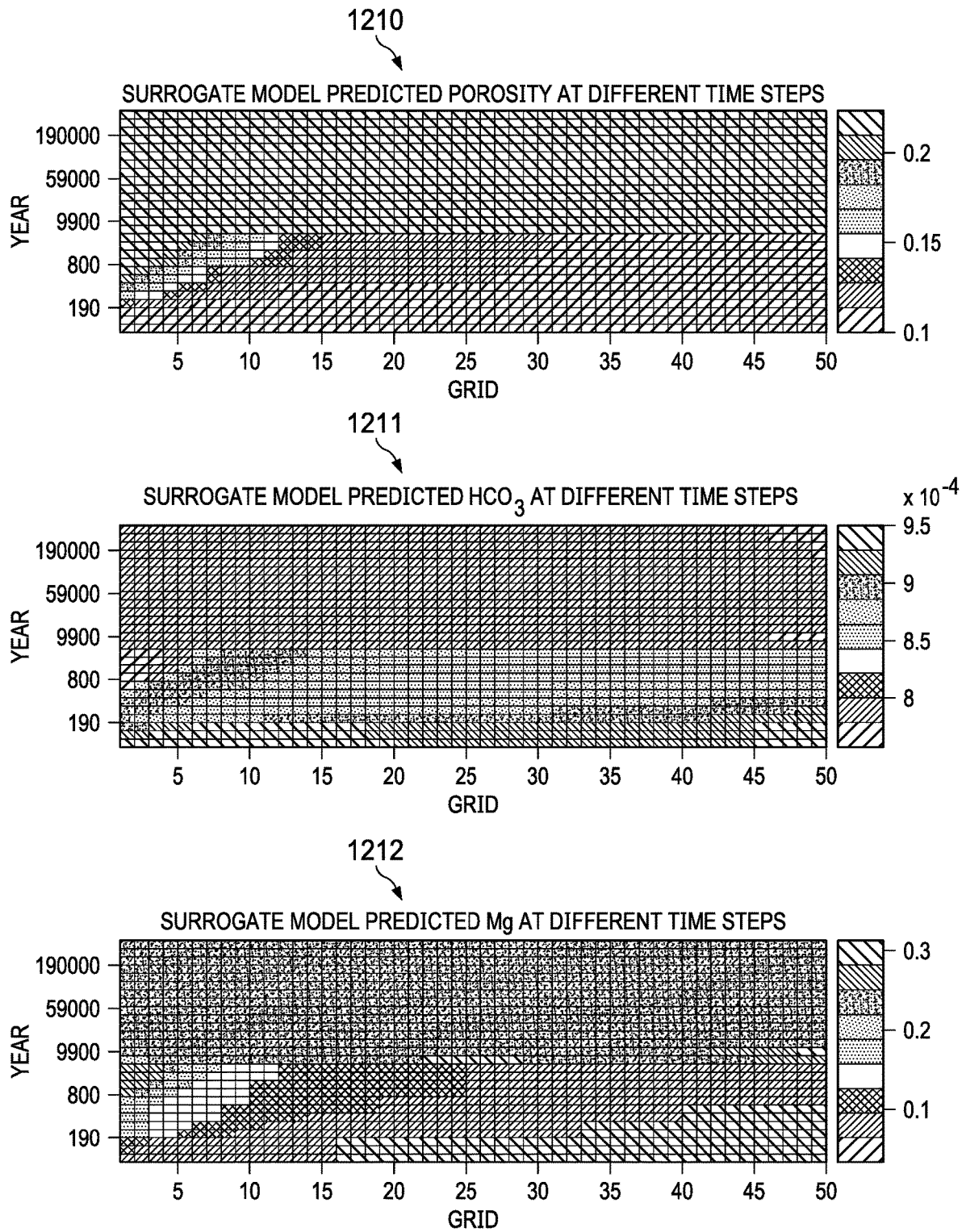
Figure 12E:
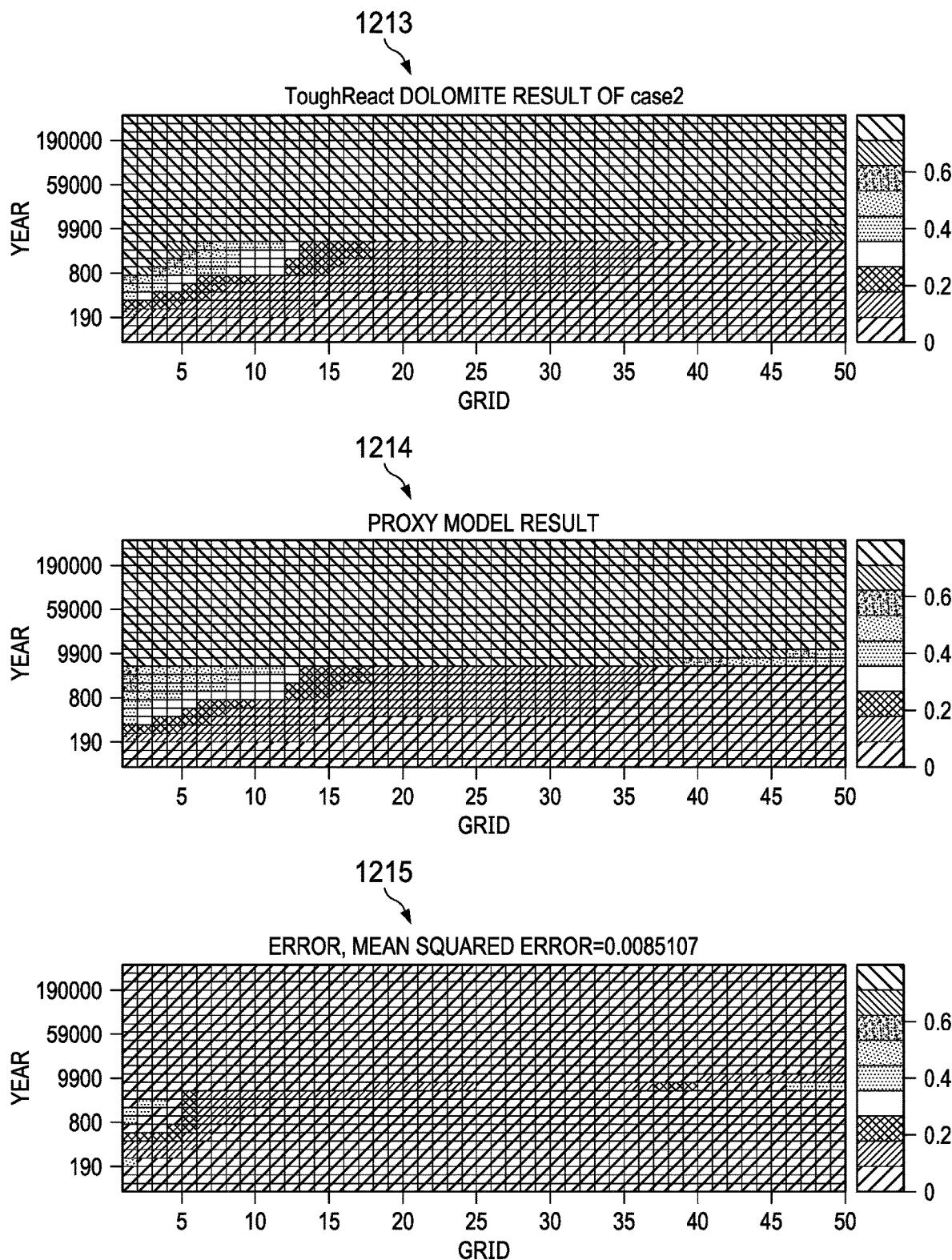
Figure 12F:
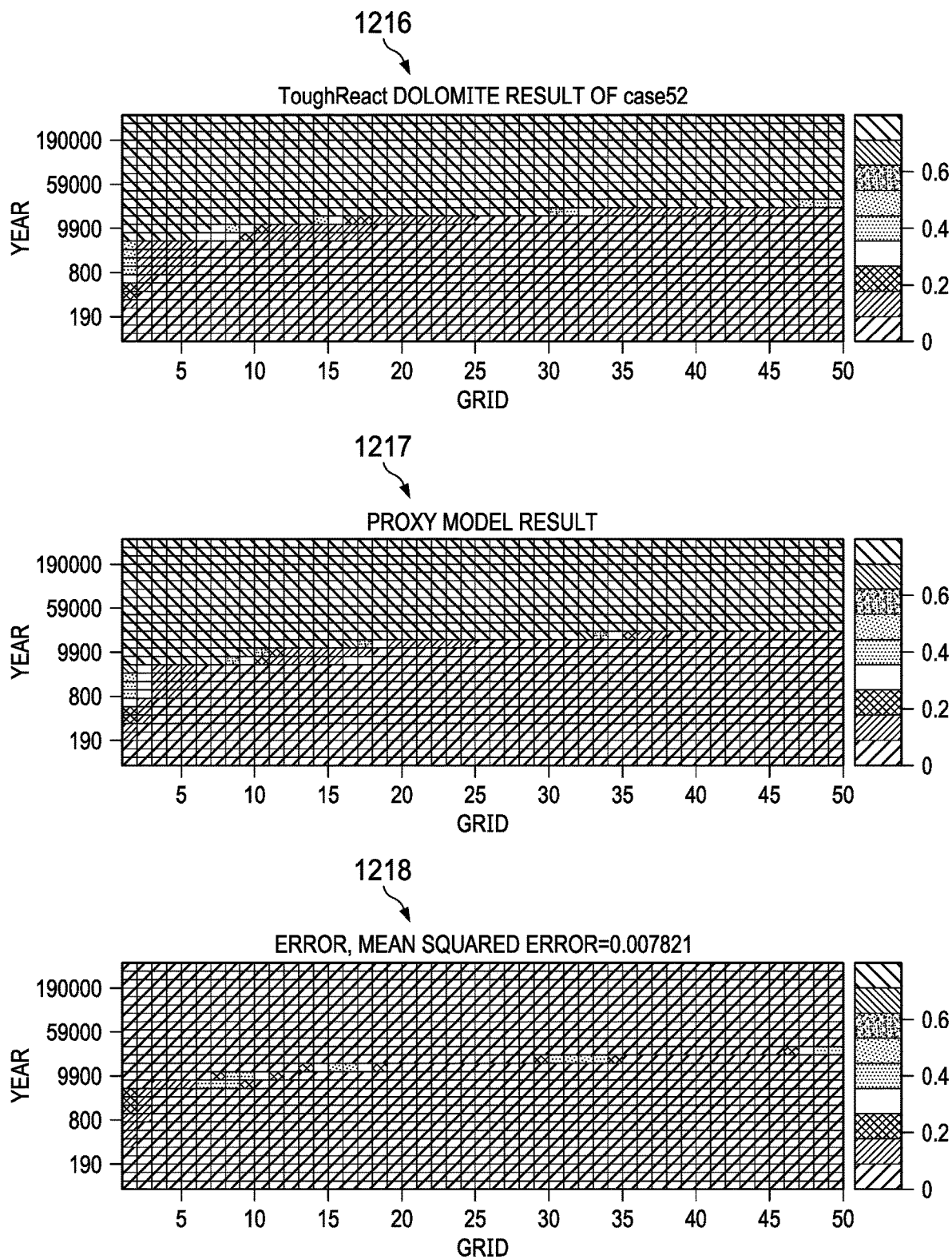

FIGS. 12A-12F are examples of UI elements 1201-1218 that are produced during execution of the UI 1000, according to some implementations of the present disclosure. Referring to FIG. 12E, the UI element 1213 is the result from original diagenetic simulation. The UI element 1214 is from the proxy model. The UI element 1215 is the error map calculated between the original simulation and proxy simulation.

Referring to FIG. 12E, the UI element 1216 is the result from original diagenetic simulation. The UI element 1217 is from the proxy model. The UI element 1218 is the error map calculated between the original simulation and proxy simulation.

Case Generation

In the GUI 1000, clicking on the control 1022 will automatically launch execution of background programs for each training case designed training cases and generated training data. The cases can be run in parallel, making use of parallel computation techniques (for example, as provided by Windows® and Linux™). The process provides an improvement over conventional techniques in which users have to write parameter file and run the training cases manually. Using the techniques described in the present disclosure, a user can run the training cases in an automatic and parallel fashion, improving user productivity and efficiency. In addition, all the cases are designed based on the LHS technique, which will ensure all the cases are representative of RTM dynamic character. The design can further ensure the training of the neural network will cover the full range of RTM character.

Neural Network Model Training

Training cases can be copied to a training cases folder, and blind test cases can be copied to a testing cases folder. Neural Network (NN) models for different output parameters can be trained separately.

In the current illustrated example, the dolomite content is recognized as the critical parameter for nested training purpose. As such, dolomite content can be modeled first. The output from the trained model can be used for other variable modeling work.

Clicking the control 1036 ("Train dolomite proxy") can result in providing an interface for selecting the destination of an output file and can initiate training of the dolomite NN model. Executing the training can cause the following to occur. From the input parameter files and the output of reactive simulator of all the training cases, the input $X=\{x^{(1)}, x^{(2)}, \ldots, x^{(n)}, s, t\}$ is extracted. The inputs include permeability and RSA, as shown in FIG. 7. From the input parameter files and the output of reactive simulator of all the training cases, the observed dolomite percentage at the target grid cells is extracted, represented by variables $Y=\{y^{(1)}, y^{(1)}, \ldots, y^{(n)}\}$. The input X and output Y are connected with the data architecture of proxy model according to the target NN model structure. The NN model is trained with the defined NN architecture. The number of neurons of the hidden layer can be specified. During the training process, the training can be stopped manually if the error does not decrease, to prevent over-fitting, as shown in FIGS. 11A-11C.

Other training buttons can be clicked one-by-one. The trained NN models are tested with completely blind case data. During testing, the blind case index corresponds to one of the cases in the testing cases folder. For testing, the controls 1054, 1056, 1058, 1060, 1062, 1064, and 1066 (for example, corresponding to "Run Dolomite test", "Run Porosity test", and so on) can be selected.

Once the well-trained models are generated, predictions can be made easily and quickly using different parameters with the additional designed case. For example, clicking control 1076 ("Run prediction with proxy") can initiate predictions based on updated parameters. Clicking control 1078 ("Run Simulation for Comparison") can initiate execution of the simulation with the updated parameters.

Figure 13:
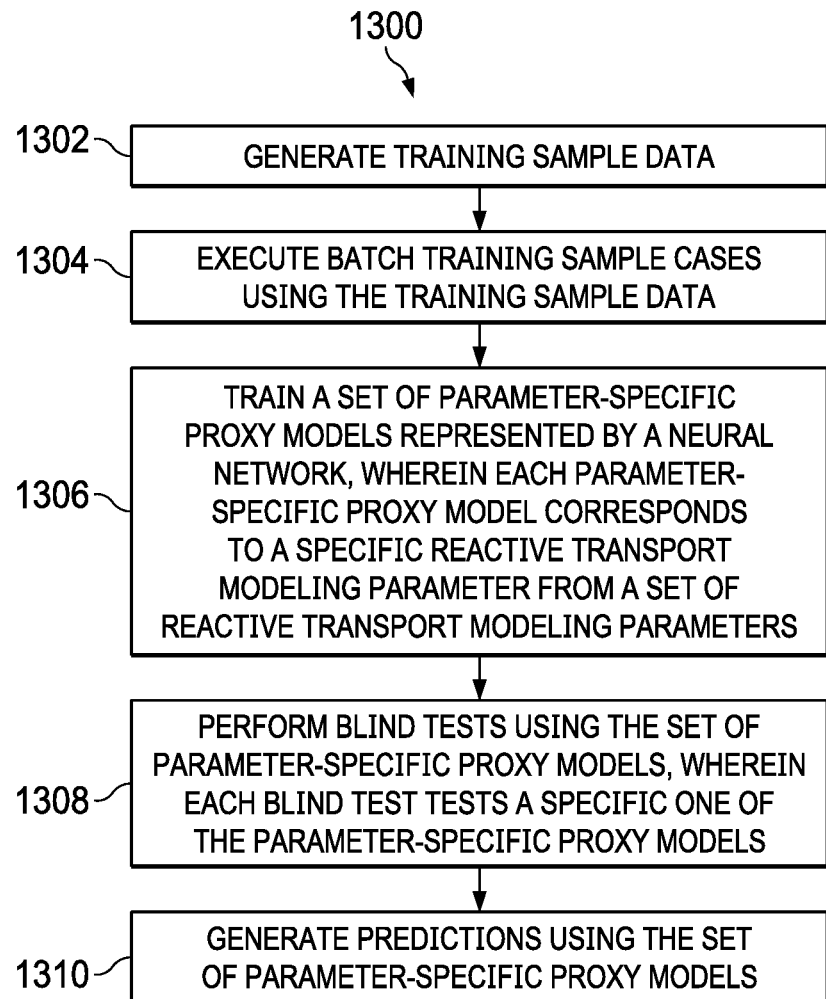
FIG. 13 is a flowchart of an example of a method for training machine learning-based proxy models as surrogates for process-based RTM, according to some implementations of the present disclosure.

FIG. 13 is a flowchart of an example of a method 1300 for training machine learning-based proxy models as surrogates for process-based RTM, according to some implementations of the present disclosure. For clarity of presentation, the description that follows generally describes method 1300 in the context of the other figures in this description. However, it will be understood that method 1300 can be performed, for example, by any suitable system, environment, software, and hardware, or a combination of systems, environments, software, and hardware, as appropriate. In some implementations, various steps of method 1300 can be run in parallel, in combination, in loops, or in any order.

At 1302, training sample data is generated. For example, the training sample data can be generated when the user clicks on the generate control 1018, initiating a program that automatically generates a spreadsheet file containing the key parameters set in each training case. Generating the training sample data can include generating parameter files based on an initial number of training cases and a number of target analysis factors, for example. From 1302, method 1300 proceeds to 1304.

At 1304, batch training sample cases are executed using the training sample data. For example, the user can initiate running of the simulation for all of the training cases using the control 1022. From 1304, method 1300 proceeds to 1306.

At 1306, a set of parameter-specific proxy models represented by a neural network is trained. Each parameter-specific proxy model corresponds to a specific RTM parameter from a set of RTM parameters. Training the set of parameter-specific proxy models can include defining training parameters for the training. The training parameters can include, for example, a training data percentage, a validate data percentage, a test data percentage, a neuron number in a first hidden layer, and a neuron number in a second hidden layer. In some implementations, the set of RTM parameters can include dolomite, porosity, permeability, pH, $Mg^{2+}$, and $Ca^{2+}$.

In some implementations, at least one parameter-specific proxy model can depend on an output of one or more previously-executed parameter-specific proxy models. For example, nested proxy models such as described with reference to FIG. 9 can exist. From 1306, method 1300 proceeds to 1308.

At 1308, blind tests are performed using the set of parameter-specific proxy models. Each blind test tests a specific one of the parameter-specific proxy models. Parameter-specific blind tests can be initiated by the user by selecting the controls 1054, 1056, 1058, 1060, 1062, and 1064. From 1308, method 1300 proceeds to 1310.

At 1310, predictions are generated using the set of parameter-specific proxy models. As an example, the user can click control 1076 ("Run prediction with proxy") to initiate predictions based on the updated parameters. After 1310, method 1300 can stop.

In some implementations, method 1300 further includes providing, for presentation to a user, a graphical user interface for providing inputs and controlling steps for training the machine learning-based proxy models as surrogates for the process-based RTM. For example, the UI 1000 can be presented to the user.

Figure 14:
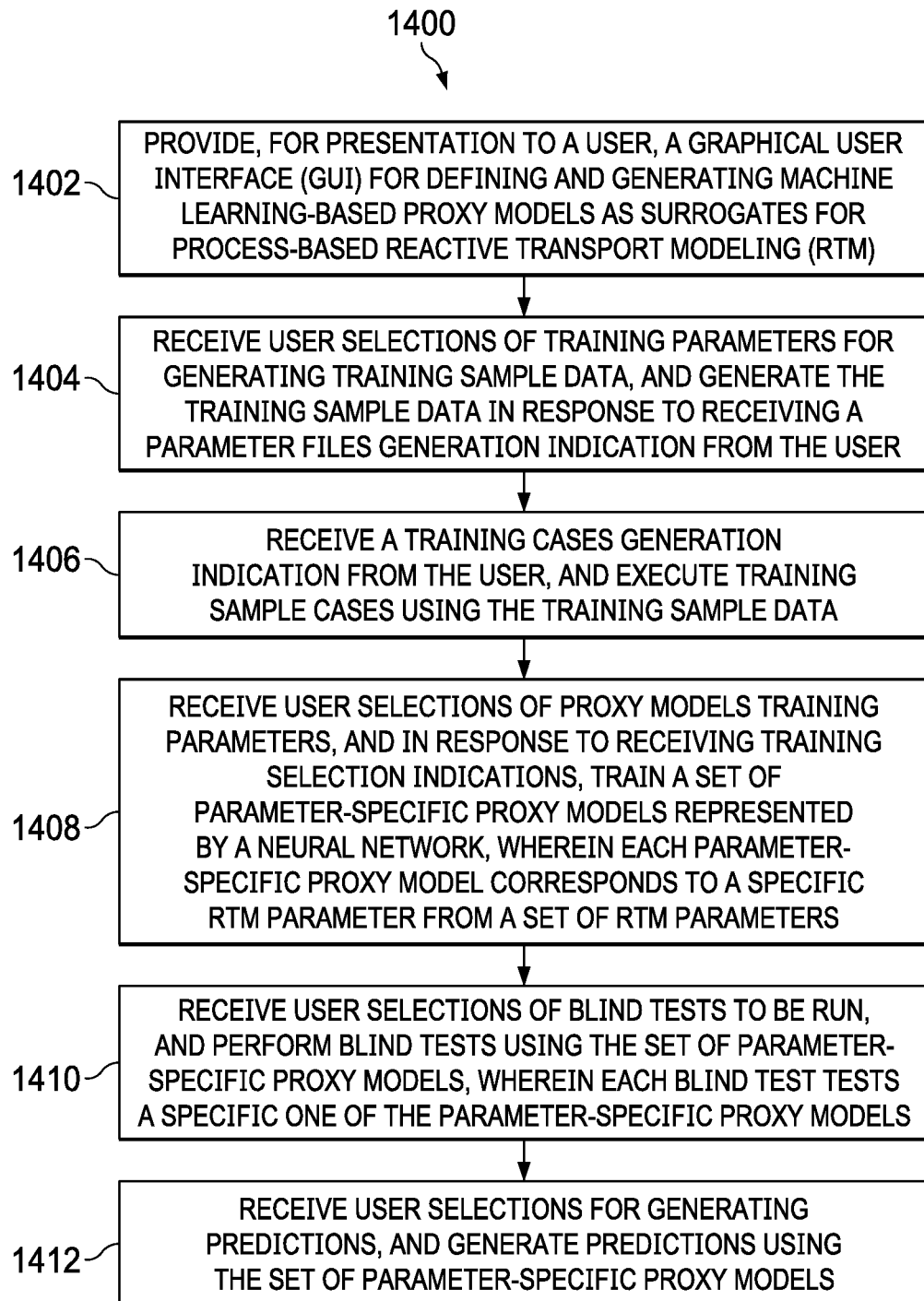
FIG. 14 is a flowchart of an example of a method for presenting and executing a user interface used for proxy models as surrogates for process-based RTM, according to some implementations of the present disclosure.

FIG. 14 is a flowchart of an example of a method 1400 for presenting and executing a user interface used for proxy models as surrogates for process-based RTM, according to some implementations of the present disclosure. For clarity of presentation, the description that follows generally describes method 1400 in the context of the other figures in this description. However, it will be understood that method 1400 can be performed, for example, by any suitable system, environment, software, and hardware, or a combination of systems, environments, software, and hardware, as appropriate. In some implementations, various steps of method 1400 can be run in parallel, in combination, in loops, or in any order.

At 1402, a graphical user interface (GUI) for defining and generating machine learning-based proxy models as surrogates for process-based reactive transport modeling (RTM) is provided for presentation to a user. For example, the UI 1000 can be presented to a user, such as a modeler or a petroleum engineer. From 1402, method 1400 proceeds to 1404.

At 1404, user selections of training parameters for generating training sample data are received. The training sample data is generated in response to receiving a parameter files generation indication from the user. For example, the user can enter information in the training sample data generation sub-panel 1002. The user can click the generate control 1018 to run the program that automatically generates a spreadsheet file containing the key parameters set in each training case. From 1404, method 1400 proceeds to 1406.

At 1406, a training cases generation indication is received from the user. Training sample cases are executed using the training sample data. For example, the user can click the control 1022 to automatically launch execution of the background programs for each training case. From 1406, method 1400 proceeds to 1408.

At 1408, user selections of proxy models training parameters are received. A set of parameter-specific proxy models represented by a neural network are trained. Each parameter-specific proxy model corresponds to a specific RTM parameter from a set of RTM parameters. For example, the user can enter information in the sub-panel 1006. The user can use controls 1036, 1038, 1040, 1042, 1044, 1046, and 1048 to initiate training on respective proxies. From 1408, method 1400 proceeds to 1410.

At 1410, user selections of blind tests to be run are received. Blind tests are performed using the set of parameter-specific proxy models. Each blind test tests a specific one of the parameter-specific proxy models. As an example, the user can complete the information in the sub-panel 1008 and then use the controls 1054, 1056, 1058, 1060, 1062, 1064, and 1066 to initiate training on respective proxies. From 1410, method 1400 proceeds to 1412.

At 1412, user selections for generating predictions are received. Predictions are generated using the set of parameter-specific proxy models. For example, the user can enter information in the sub-panel 1010 and then use the controls 1074, 1076, and 1078 to perform additional actions, including making predictions. After 1412, method 1400 can stop.

For the 2D or 3D case, in order to reduce the computing time, not all model cells are put into the neural network. For example, randomly-picked model cells (or "observation cells") can be used in the neural network. For example, a workflow corresponding to the method 1500 can be used.

In some implementations, approximately 1000 cells can be regarded as a normal 1D case. If the cells number is more than 100, for example, then the cells can be simplified using the proposed methodology in 2D or 3D case as described with reference to FIG. 15.

For 2D or 3D case, or when there is huge number of cells in 1D case, the training data set can be extremely large if all of the spatial locations are used. A random sampling scheme can reduce the size of the data set. Within the x and y limits of a 2D geographic space and cells definition, the cells can be picked randomly to form a training data set. A 2D case, as an example to illustrate the spatial locations of cell picking, is shown in FIG. 5.

In some implementations, the random picking scheme for the 2D/3D case can be written in pseudo-code such as:

```
Input: x and y limit of the model, picking total number
    Order all the cells of the 2D/3D model;
    Randomly produce an array with size equal to picking total number;
    Order the original cells index array according to the random array;
    From 1 to the picking number of the new-ordered cells array are the picked cells
Output: the cell index with range of picked total number.
```

After building a satisfied proxy model with those cells, the values for other cells in the proxy model can be interpolated from those randomly-picked cells. Any suitable spatial interpolation algorithms (for example, kriging) can be used.

Figure 15:
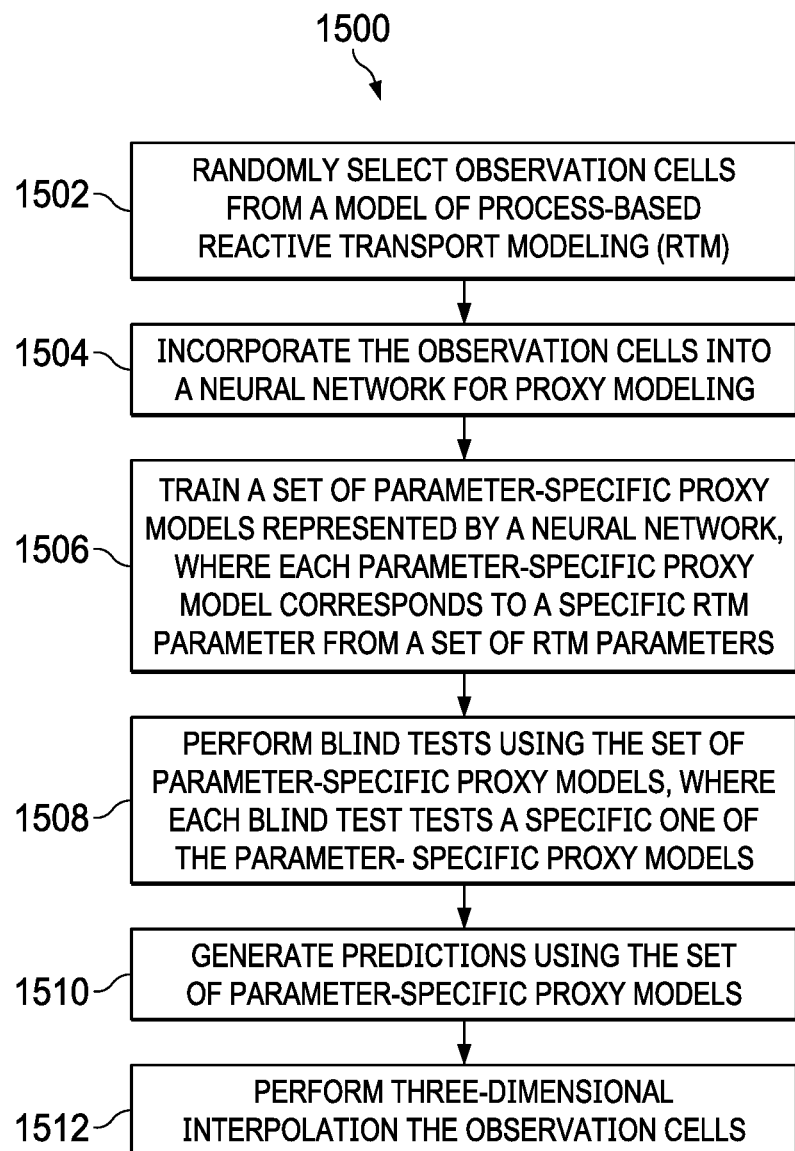
FIG. 15 is a flowchart of an example of a method for random selection of observation cells for proxy modeling of reactive transport modeling, according to some implementations of the present disclosure.

FIG. 15 is a flowchart of an example of a method 1500 for random selection of observation cells for proxy modeling of reactive transport modeling, according to some implementations of the present disclosure. For clarity of presentation, the description that follows generally describes method 1500 in the context of the other figures in this description. However, it will be understood that method 1500 can be performed, for example, by any suitable system, environment, software, and hardware, or a combination of systems, environments, software, and hardware, as appropriate. In some implementations, various steps of method 1500 can be run in parallel, in combination, in loops, or in any order.

At 1502, observation cells are randomly selected from a model of process-based reactive transport modeling (RTM). For example, sample spatial locations 501-510 of cell picking can be selected for parameters $s_1$ through $s_{10}$, respectively. From 1502, method 1500 proceeds to 1504.

At 1504, the observation cells are incorporated into a neural network for proxy modeling. As an example, the spatial locations 501-510 can be used in the nested neural network architecture 900. From 1504, method 1500 proceeds to 1506.

At 1506, a set of parameter-specific proxy models represented by a neural network is trained. Each parameter-specific proxy model corresponds to a specific RTM parameter from a set of RTM parameters. As an example, models corresponding to controls 1036, 1038, 1040, 1042, 1044, 1046, and 1048 can be trained for respective proxies. From 1506, method 1500 proceeds to 1508.

At 1508, blind tests are performed using the set of parameter-specific proxy models, where each blind test tests a specific one of the parameter-specific proxy models. As an example, blind testing of the models for the respective proxies corresponding to the controls 1054, 1056, 1058, 1060, 1062, 1064, and 1066 can be initiated. From 1508, method 1500 proceeds to 1510.

At 1510, predictions are generated using the set of parameter-specific proxy models. For example, the user can use the control 1076, and 1078 to make predictions. From 1510, method 1500 proceeds to 1512.

At 1512, 3-dimensional interpolation the observation cells is performed. As an example, a 3D interpolation of cells represented by the 2D sample spatial locations 501-510 can occur. A stack of 2D samples can represent the 3D case, for example. After 1512, method 1500 can stop.

Figure 16:
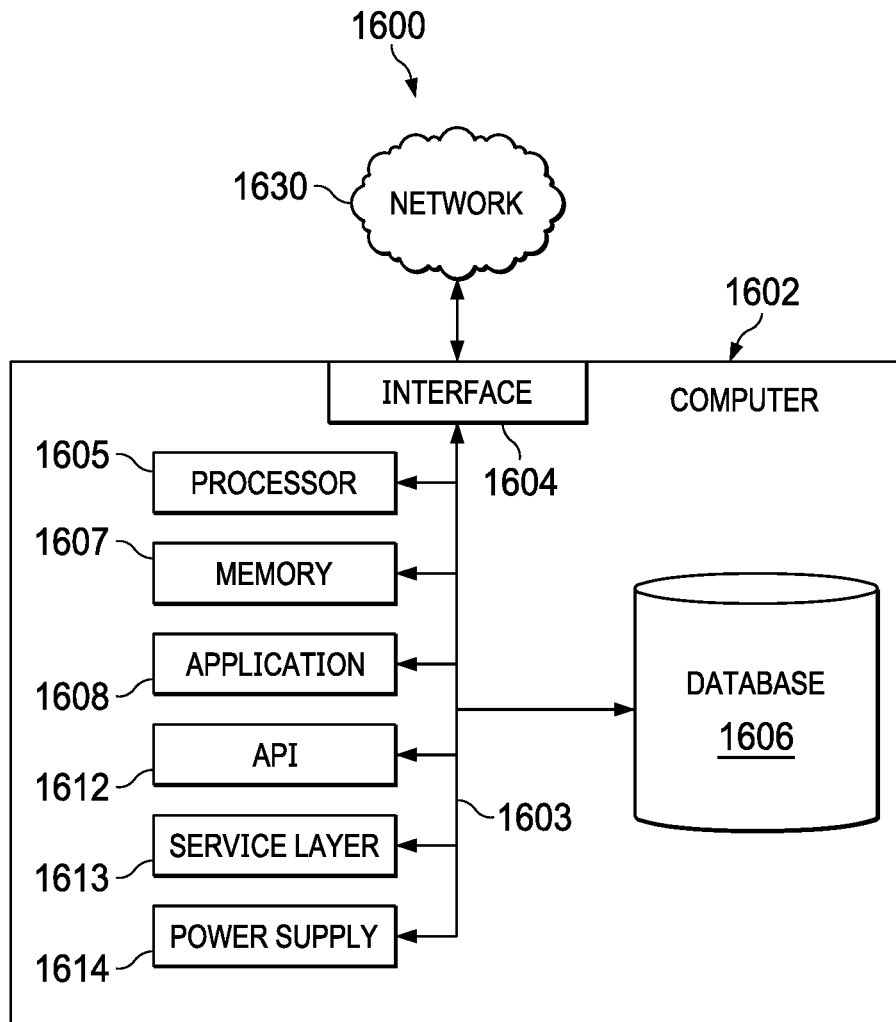
FIG. 16 is a block diagram illustrating an example computer system used to provide computational functionalities associated with described algorithms, methods, functions, processes, flows, and procedures as described in the present disclosure, according to some implementations of the present disclosure.

FIG. 16 is a block diagram of an example computer system 1600 used to provide computational functionalities associated with described algorithms, methods, functions, processes, flows, and procedures described in the present disclosure, according to some implementations of the present disclosure. The illustrated computer 1602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1602 can include input devices such as keypads, keyboards, and touch screens that can accept user information. Also, the computer 1602 can include output devices that can convey information associated with the operation of the computer 1602. The information can include digital data, visual data, audio information, or a combination of information. The information can be presented in a graphical user interface (UI) (or GUI).

The computer 1602 can serve in a role as a client, a network component, a server, a database, a persistency, or components of a computer system for performing the subject matter described in the present disclosure. The illustrated computer 1602 is communicably coupled with a network 1630. In some implementations, one or more components of the computer 1602 can be configured to operate within different environments, including cloud-computing-based environments, local environments, global environments, and combinations of environments.

At a top level, the computer 1602 is an electronic computing device operable to receive, transmit, process, store, and manage data and information associated with the described subject matter. According to some implementations, the computer 1602 can also include, or be communicably coupled with, an application server, an email server, a web server, a caching server, a streaming data server, or a combination of servers.

The computer 1602 can receive requests over network 1630 from a client application (for example, executing on another computer 1602). The computer 1602 can respond to the received requests by processing the received requests using software applications. Requests can also be sent to the computer 1602 from internal users (for example, from a command console), external (or third) parties, automated applications, entities, individuals, systems, and computers.

Each of the components of the computer 1602 can communicate using a system bus 1603. In some implementations, any or all of the components of the computer 1602, including hardware or software components, can interface with each other or the interface 1604 (or a combination of both) over the system bus 1603. Interfaces can use an application programming interface (API) 1612, a service layer 1613, or a combination of the API 1612 and service layer 1613. The API 1612 can include specifications for routines, data structures, and object classes. The API 1612 can be either computer-language independent or dependent. The API 1612 can refer to a complete interface, a single function, or a set of APIs.

The service layer 1613 can provide software services to the computer 1602 and other components (whether illustrated or not) that are communicably coupled to the computer 1602. The functionality of the computer 1602 can be accessible for all service consumers using this service layer. Software services, such as those provided by the service layer 1613, can provide reusable, defined functionalities through a defined interface. For example, the interface can be software written in JAVA, C++, or a language providing data in extensible markup language (XML) format. While illustrated as an integrated component of the computer 1602, in alternative implementations, the API 1612 or the service layer 1613 can be stand-alone components in relation to other components of the computer 1602 and other components communicably coupled to the computer 1602. Moreover, any or all parts of the API 1612 or the service layer 1613 can be implemented as child or sub-modules of another software module, enterprise application, or hardware module without departing from the scope of the present disclosure.

The computer 1602 includes an interface 1604. Although illustrated as a single interface 1604 in FIG. 16, two or more interfaces 1604 can be used according to particular needs, desires, or particular implementations of the computer 1602 and the described functionality. The interface 1604 can be used by the computer 1602 for communicating with other systems that are connected to the network 1630 (whether illustrated or not) in a distributed environment. Generally, the interface 1604 can include, or be implemented using, logic encoded in software or hardware (or a combination of software and hardware) operable to communicate with the network 1630. More specifically, the interface 1604 can include software supporting one or more communication protocols associated with communications. As such, the network 1630 or the interface's hardware can be operable to communicate physical signals within and outside of the illustrated computer 1602.

The computer 1602 includes a processor 1605. Although illustrated as a single processor 1605 in FIG. 16, two or more processors 1605 can be used according to particular needs, desires, or particular implementations of the computer 1602 and the described functionality. Generally, the processor 1605 can execute instructions and can manipulate data to perform the operations of the computer 1602, including operations using algorithms, methods, functions, processes, flows, and procedures as described in the present disclosure.

The computer 1602 also includes a database 1606 that can hold data for the computer 1602 and other components connected to the network 1630 (whether illustrated or not). For example, database 1606 can be an in-memory, conventional, or a database storing data consistent with the present disclosure. In some implementations, database 1606 can be a combination of two or more different database types (for example, hybrid in-memory and conventional databases) according to particular needs, desires, or particular implementations of the computer 1602 and the described functionality. Although illustrated as a single database 1606 in FIG. 16, two or more databases (of the same, different, or combination of types) can be used according to particular needs, desires, or particular implementations of the computer 1602 and the described functionality. While database 1606 is illustrated as an internal component of the computer 1602, in alternative implementations, database 1606 can be external to the computer 1602.

The computer 1602 also includes a memory 1607 that can hold data for the computer 1602 or a combination of components connected to the network 1630 (whether illustrated or not). Memory 1607 can store any data consistent with the present disclosure. In some implementations, memory 1607 can be a combination of two or more different types of memory (for example, a combination of semiconductor and magnetic storage) according to particular needs, desires, or particular implementations of the computer 1602 and the described functionality. Although illustrated as a single memory 1607 in FIG. 16, two or more memories 1607 (of the same, different, or combination of types) can be used according to particular needs, desires, or particular implementations of the computer 1602 and the described functionality. While memory 1607 is illustrated as an internal component of the computer 1602, in alternative implementations, memory 1607 can be external to the computer 1602.

The application 1608 can be an algorithmic software engine providing functionality according to particular needs, desires, or particular implementations of the computer 1602 and the described functionality. For example, application 1608 can serve as one or more components, modules, or applications. Further, although illustrated as a single application 1608, the application 1608 can be implemented as multiple applications 1608 on the computer 1602. In addition, although illustrated as internal to the computer 1602, in alternative implementations, the application 1608 can be external to the computer 1602.

The computer 1602 can also include a power supply 1614. The power supply 1614 can include a rechargeable or non-rechargeable battery that can be configured to be either user- or non-user-replaceable. In some implementations, the power supply 1614 can include power-conversion and management circuits, including recharging, standby, and power management functionalities. In some implementations, the power-supply 1614 can include a power plug to allow the computer 1602 to be plugged into a wall socket or a power source to, for example, power the computer 1602 or recharge a rechargeable battery.

There can be any number of computers 1602 associated with, or external to, a computer system containing computer 1602, with each computer 1602 communicating over network 1630. Further, the terms "client," "user," and other appropriate terminology can be used interchangeably, as appropriate, without departing from the scope of the present disclosure. Moreover, the present disclosure contemplates that many users can use one computer 1602 and one user can use multiple computers 1602.

Described implementations of the subject matter can include one or more features, alone or in combination.

For example, in a first implementation, a computer-implemented method for random selection and use of observation cells includes the following. Observation cells are randomly selected from a model of process-based reactive transport modeling (RTM). The observation cells are incorporated into a neural network for proxy modeling. A set of parameter-specific proxy models represented by a neural network is trained. Each parameter-specific proxy model corresponds to a specific RTM parameter from a set of RTM parameters. Blind tests are performed using the set of parameter-specific proxy models, where each blind test tests a specific one of the parameter-specific proxy models. Predictions are generated using the set of parameter-specific proxy models. 3-dimensional interpolation the observation cells is performed.

The foregoing and other described implementations can each, optionally, include one or more of the following features:

A first feature, combinable with any of the following features, the method further including generating training sample data; and executing training sample cases using the training sample data.

A second feature, combinable with any of the previous or following features, the method further including generating predictions using the set of parameter-specific proxy models and interpolated values.

A third feature, combinable with any of the previous or following features, where generating the training sample data includes generating parameter files based on an initial number of training cases and a number of target analysis factors.

A fourth feature, combinable with any of the previous or following features, where the set of RTM parameters includes one or more of dolomite, porosity, permeability, pH, magnesium ions ($Mg^{2+}$), and calcium ions ($Ca^{2+}$).

A fifth feature, combinable with any of the previous or following features, where training the set of parameter-specific proxy models includes defining training parameters for the training.

A sixth feature, combinable with any of the previous or following features, where the training parameters include a training data percentage, a validate data percentage, a test data percentage, a neuron number in a first hidden layer, and a neuron number in a second hidden layer.

In a second implementation, a non-transitory, computer-readable medium stores one or more instructions executable by a computer system to perform operations for random selection and use of observation cells including the following. Observation cells are randomly selected from a model of process-based reactive transport modeling (RTM). The observation cells are incorporated into a neural network for proxy modeling. A set of parameter-specific proxy models represented by a neural network is trained. Each parameter-specific proxy model corresponds to a specific RTM parameter from a set of RTM parameters. Blind tests are performed using the set of parameter-specific proxy models, where each blind test tests a specific one of the parameter-specific proxy models. Predictions are generated using the set of parameter-specific proxy models. 3-dimensional interpolation the observation cells is performed.

The foregoing and other described implementations can each, optionally, include one or more of the following features:

A first feature, combinable with any of the following features, the operations further including generating training sample data; and executing training sample cases using the training sample data.

A second feature, combinable with any of the previous or following features, the operations further including generating predictions using the set of parameter-specific proxy models and interpolated values.

A third feature, combinable with any of the previous or following features, where generating the training sample data includes generating parameter files based on an initial number of training cases and a number of target analysis factors.

A fourth feature, combinable with any of the previous or following features, where the set of RTM parameters includes one or more of dolomite, porosity, permeability, pH, magnesium ions ($Mg^{2+}$), and calcium ions (Ca').

A fifth feature, combinable with any of the previous or following features, where training the set of parameter-specific proxy models includes defining training parameters for the training.

A sixth feature, combinable with any of the previous or following features, where the training parameters include a training data percentage, a validate data percentage, a test data percentage, a neuron number in a first hidden layer, and a neuron number in a second hidden layer.

In a third implementation, a computer-implemented system includes one or more processors and a non-transitory computer-readable storage medium coupled to the one or more processors and storing programming instructions for execution by the one or more processors, the programming instructions instructing the one or more processors to perform operations for random selection and use of observation cells including the following. Observation cells are randomly selected from a model of process-based reactive transport modeling (RTM). The observation cells are incorporated into a neural network for proxy modeling. A set of parameter-specific proxy models represented by a neural network is trained. Each parameter-specific proxy model corresponds to a specific RTM parameter from a set of RTM parameters. Blind tests are performed using the set of parameter-specific proxy models, where each blind test tests a specific one of the parameter-specific proxy models. Predictions are generated using the set of parameter-specific proxy models. 3-dimensional interpolation the observation cells is performed.

The foregoing and other described implementations can each, optionally, include one or more of the following features:

A first feature, combinable with any of the following features, the operations further including generating training sample data; and executing training sample cases using the training sample data.

A second feature, combinable with any of the previous or following features, the operations further including generating predictions using the set of parameter-specific proxy models and interpolated values.

A third feature, combinable with any of the previous or following features, where generating the training sample data includes generating parameter files based on an initial number of training cases and a number of target analysis factors.

A fourth feature, combinable with any of the previous or following features, where the set of RTM parameters includes one or more of dolomite, porosity, permeability, pH, magnesium ions $Mg^{2+}$), and calcium ions ($Ca^{2+}$).

A fifth feature, combinable with any of the previous or following features, where training the set of parameter-specific proxy models includes defining training parameters for the training.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/-R, DVD-RAM, DVD-ROM, HD-DVD, and BLU-RAY.

The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure.

Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method comprising:
    randomly selecting observation cells from a model of process-based reactive transport modeling (RTM);
    incorporating the observation cells into a neural network for proxy modeling;
    receiving, through a user interface, selections of training parameters for training a set of parameter-specific proxy models;
    training, using the selections of training parameters, a set of parameter-specific proxy models represented by a neural network, wherein each parameter-specific proxy model corresponds to a specific RTM parameter from a set of RTM parameters;
    performing tests using the set of parameter-specific proxy models, wherein each test tests a specific one of the parameter-specific proxy models;
    generating predictions using the set of parameter-specific proxy models, wherein generating the predictions includes using nested prediction strategies including:
        predicting, using the specific RTM parameter, a critical observation variable; and
        predicting, using the critical observation variable, another observation variable;
    performing 3-dimensional interpolation of the observation cells; and
    generating, using results of multiple execution iterations of the parameter-specific proxy model, a progress sub-panel in a user interface, wherein the progress sub-panel identifies at least a number of completed iterations and a performance value corresponding to a mean squared error achieved by each iteration.

2. The computer-implemented method of claim 1, further comprising:
    generating training sample data; and
    executing training sample cases using the training sample data.

3. The computer-implemented method of claim 1, further comprising:
    generating predictions using the set of parameter-specific proxy models and interpolated values.

4. The computer-implemented method of claim 2, wherein generating the training sample data includes generating parameter files based on an initial number of training cases and a number of target analysis factors.

5. The computer-implemented method of claim 1, wherein the set of RTM parameters comprises one or more of dolomite, porosity, permeability, pH, magnesium ions ($Mg^{2+}$), and calcium ions ($Ca^{2+}$).

6. The computer-implemented method of claim 1, wherein training the set of parameter-specific proxy models includes defining training parameters for the training.

7. The computer-implemented method of claim 6, wherein the training parameters include a training data percentage, a validate data percentage, a test data percentage, a neuron number in a first hidden layer, and a neuron number in a second hidden layer.

8. A non-transitory, computer-readable medium storing one or more instructions executable by a computer system to perform operations comprising:
    randomly selecting observation cells from a model of process-based reactive transport modeling (RTM);
    incorporating the observation cells into a neural network for proxy modeling;
    receiving, through a user interface, selections of training parameters for training a set of parameter-specific proxy models;
    training, using the selections of training parameters, a set of parameter-specific proxy models represented by a neural network, wherein each parameter-specific proxy model corresponds to a specific RTM parameter from a set of RTM parameters;
    performing tests using the set of parameter-specific proxy models, wherein each test tests a specific one of the parameter-specific proxy models;
    generating predictions using the set of parameter-specific proxy models, wherein generating the predictions includes using nested prediction strategies including:
        predicting, using the specific RTM parameter, a critical observation variable; and
        predicting, using the critical observation variable, another observation variable;
    performing 3-dimensional interpolation of the observation cells; and
    generating, using results of multiple execution iterations of the parameter-specific proxy model, a progress sub-panel in a user interface, wherein the progress sub-panel identifies at least a number of completed iterations and a performance value corresponding to a mean squared error achieved by each iteration.

9. The non-transitory, computer-readable medium of claim 8, the operations further comprising:
    generating training sample data; and
    executing training sample cases using the training sample data.

10. The non-transitory, computer-readable medium of claim 8, the operations further comprising:
    generating predictions using the set of parameter-specific proxy models and interpolated values.

11. The non-transitory, computer-readable medium of claim 9, wherein generating the training sample data includes generating parameter files based on an initial number of training cases and a number of target analysis factors.

12. The non-transitory, computer-readable medium of claim 8, wherein the set of RTM parameters comprises one or more of dolomite, porosity, permeability, pH, magnesium ions $Mg^{2+}$), and calcium ions ($Ca^{2+}$).

13. The non-transitory, computer-readable medium of claim 8, wherein training the set of parameter-specific proxy models includes defining training parameters for the training.

14. The non-transitory, computer-readable medium of claim 13, wherein the training parameters include a training data percentage, a validate data percentage, a test data percentage, a neuron number in a first hidden layer, and a neuron number in a second hidden layer.

15. A computer-implemented system, comprising:
    one or more processors; and
    a non-transitory computer-readable storage medium coupled to the one or more processors and storing programming instructions for execution by the one or more processors, the programming instructions instructing the one or more processors to perform operations comprising:
        randomly selecting observation cells from a model of process-based reactive transport modeling (RTM);
        incorporating the observation cells into a neural network for proxy modeling;
        receiving, through a user interface, selections of training parameters for training a set of parameter-specific proxy models;
        training, using the selections of training parameters, a set of parameter-specific proxy models represented by a neural network, wherein each parameter-specific proxy model corresponds to a specific RTM parameter from a set of RTM parameters;
        performing tests using the set of parameter-specific proxy models, wherein each test tests a specific one of the parameter-specific proxy models;
        generating predictions using the set of parameter-specific proxy models, wherein generating the predictions includes using nested prediction strategies including:
            predicting, using the specific RTM parameter, a critical observation variable; and
            predicting, using the critical observation variable, another observation variable;
        performing 3-dimensional interpolation of the observation cells; and
        generating, using results of multiple execution iterations of the parameter-specific proxy model, a progress sub-panel in a user interface, wherein the progress sub-panel identifies at least a number of completed iterations and a performance value corresponding to a mean squared error achieved by each iteration.

16. The computer-implemented system of claim 15, the operations further comprising:
    generating training sample data; and
    executing training sample cases using the training sample data.

17. The computer-implemented system of claim 15, the operations further comprising:
    generating predictions using the set of parameter-specific proxy models and interpolated values.

18. The computer-implemented system of claim 16, wherein generating the training sample data includes generating parameter files based on an initial number of training cases and a number of target analysis factors.

19. The computer-implemented system of claim 15, wherein the set of RTM parameters comprises one or more of dolomite, porosity, permeability, pH, magnesium ions ($Mg^{2+}$), and calcium ions ($Ca^{2+}$).

20. The computer-implemented system of claim 15, wherein training the set of parameter-specific proxy models includes defining training parameters for the training.

* * * * *